United States Patent
Hawthorne et al.

(10) Patent No.: US 6,274,116 B1
(45) Date of Patent: Aug. 14, 2001

(54) COMPOSITIONS FOR BORON DELIVERY TO MAMMALIAN TISSUE

(75) Inventors: M. Frederick Hawthorne, Encino; Debra Arlene Feaks; Kenneth John Shelly, both of Los Angeles, all of CA (US)

(73) Assignee: Reagents of the University of California, Oakland, CA (US)

( * ) Notice: Subject to any disclaimer, the term of this patent is extended or adjusted under 35 U.S.C. 154(b) by 0 days.

(21) Appl. No.: 09/280,098

(22) Filed: Mar. 29, 1999

Related U.S. Application Data

(60) Continuation-in-part of application No. 08/511,073, filed on Aug. 3, 1995, now Pat. No. 5,888,473, which is a division of application No. 08/074,702, filed on Jun. 3, 1993, now Pat. No. 5,648,532.

(51) Int. Cl.[7] ............................. A61K 51/00; A61K 9/127
(52) U.S. Cl. ........................................... 424/1.21; 424/450
(58) Field of Search ................................... 424/1.21, 450, 424/657; 514/64; 556/7, 8; 568/3, 4

(56) References Cited

U.S. PATENT DOCUMENTS

| | | | |
|---|---|---|---|
| 5,272,250 | * 12/1993 | Spielvogel et al. | 530/300 |
| 5,328,678 | * 7/1994 | Fujii et al. | 424/1.21 |
| 5,856,551 | * 1/1999 | Kane et al. | 558/72 |

FOREIGN PATENT DOCUMENTS

92/22298 * 12/1992 (WO) ............................. A61K/31/47

OTHER PUBLICATIONS

Shelly K. et al., Model studies directed toward the boron neutron–capture therapy of cancer, Proc. Natl. Acad. Sci., vol. 89, pp. 9039–9043, Oct. 1992.*

* cited by examiner

*Primary Examiner*—Michael G. Hartley
(74) *Attorney, Agent, or Firm*—Koppel & Jacobs; Michael J. Ram

(57) ABSTRACT

Boron neutron capture therapy can utilize $X_y B_{20} H_{17} L$ where X is an alkali metal, y is 1 to 4, and L is a two electron donor such as $NH_3$, and $Na_2 B_{10} H_9 NCO$, among others. These borane salts may be used free or encapsulated in liposomes. Liposomes may also have embedded within their bilayers carboranes to increase the amount of delivered $^{10}B$ and/or to increase the tumor specificity of the liposome.

24 Claims, 15 Drawing Sheets

COMPOSITIONS FOR BORON DELIVERY TO MAMMALIAN TISSUE

This application is a continuation-in-part of U.S. Ser. No. 08/511,073 filed Aug. 3, 1995, now U.S. Pat. No. 5,888,473 which is a divisional of 08/071,702 filed Jun. 3, 1993, now U.S. Pat. No. 5,648,532.

This invention was made with support under Grant Number DE-FG03-95ER 61975 from the Department of Energy. Accordingly, the U.S. Government has certain rights in the invention.

FIELD OF THE INVENTION

This invention generally relates to compositions and methods for treating tumors, and more particularly to compositions and methods for treating tumors using borane derivatives both free and liposome encapsulated.

BACKGROUND OF THE INVENTION

Neutron capture therapy is an attractive method for cancer therapy, specifically the treatment of malignant tumors. The generalized reaction involves capture of a thermalized neutron (usually from a nuclear reactor with special moderators and ports) by an appropriate nucleus having a large neutron capture cross-section. The subsequent decay emits energetic particles (alpha particles) which can kill nearby tumor cells. Since the energetic and cytotoxic alpha particles travel only about one cell diameter in tissue, preferably one may specify the cell type to be destroyed by placing the alpha particle precursors only on or within the tumor cells.

Boron-10 (also designated as $^{10}B$), for example, has such an appropriate nucleus and has particularly advantageous properties for this scheme. The boron-10/thermal neutron capture reaction is as follows (* indicating an unstable intermediate state of the boron nucleus):

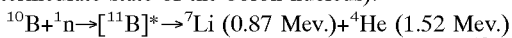

$$^{10}B + ^{1}n \rightarrow [^{11}B]^* \rightarrow ^{7}Li \ (0.87 \ Mev.) + ^{4}He \ (1.52 \ Mev.)$$

In order for this therapy to be effective, sufficient $^{10}B$ must be localized in a tumor to generate the required density of particles. This level has been variously estimated to be approximately 10–50 $\mu g$ $^{10}B/gm$ tumor. Furthermore, the concentration of $^{10}B$ in normal tissue and blood should be limited and preferably less than the concentration in the tumor in order to minimize damage to healthy cells and blood vessels. H. Hatanaka (1986) Boron-Neutron Capture Therapy for Tumors; Nishimura Co., Ltd. p. 1–16.

Large numbers of boron containing compounds have been tested for their ability to satisfy the above criteria. With few exceptions, all have failed as not enough boron has localized in the tumor and the concentration in the blood has been too high for effective neutron capture therapy. Human clinical trials with $Na_2B_{12}H_{11}SH$ in Japan have shown some promise, but only for a limited group of brain tumors. Id. 16–26.

Neutron capture therapy would be greatly expanded in usefulness if a generalized method for delivering high concentrations of $^{10}B$ to tumors were available. It would further be useful if more $^{10}B$ collected in tumor than in the blood.

Recently it has become possible to deliver drugs and other compounds selectively to tumors using liposomes of a particular composition structure. See European Patent Application No. 87311040.7 published Jun. 22, 1988; U.S. Pat. No. 5,019,369 to Presant; and "Liposomes from Biophysics to Therapeutics", M. J. Ostro, Ed., Marcel Dekker, Inc., New York (1987), all of which are incorporated herein by reference.

Incorporation of compounds with higher osmolarity inside the internal space of liposomes than outside, as is necessary for effective neutron capture therapy, depends on incorporating the highest concentration of $^{10}B$ possible without substantially altering the liposome's favorable biodistribution characteristics. Thus, the objective of at least 10 $\mu g$ $^{10}B$ per gram of tumor tissue can be met (assuming use of greater than 90% $^{10}B$ enriched material).

$Na_2B_{20}H_{18}$ and its hydroxide derivatives are known. See M. F. Hawthorne, R. L. Pilling, and P. M. Garrett, J. Am. Chem. Soc. 87, 4740 (1965). It is known to use boron containing polyphosphonates for the treatment of calcific tumors. See European Patent Application No. 82200784.5 published May 1, 1983. Boronated porphyrin compounds for use in neutron capture therapy are also known. See U.S. Pat. No. 4,959,356 to Miura, U.S. Pat. No. 5,116,980 to Gabel and U.S. Pat. No. 4,466,952 to Hadd.

There is a continuing long felt but unmet need for a method of selectively delivering therapeutic concentrations of $^{10}B$ to tumors. There is a similar need for $^{10}B$ compositions and delivery vehicles which can be used in boron neutron capture therapy.

OBJECT OF THE INVENTION

It is an object of the invention to provide compositions and methods for delivering therapeutically useful concentrations of boron containing compounds to tumors for use in neutron capture tumor therapy.

It is a further object to provide borane and liposome encapsulated borane compounds that have the properties of retaining concentrations of said borane compounds inside the liposomes without significant breakage of the liposomes.

It is a further object of the invention to provide a method of cancer therapy through use of both free and liposomal encapsulated borane compounds with the means to deliver at least 10 micrograms $^{10}B$ per gram of tumor tissue to animal and human tumors, while minimizing the concentration of $^{10}B$ in the blood.

SUMMARY OF THE PREFERRED EMBODIMENTS

The above objectives are fulfilled by the present invention. In one aspect of the present invention therapeutically effective borane derivatives having two electron donors on the borane cage are encapsulated within the internal aqueous space of liposomes, and the liposomes thereafter administered to a tumor bearing patient. In another aspect of the present invention, certain free boranes useful for neutron capture therapy have been found to have favorable biodistributions. Preferably both free and liposome encapsulated $Na_3B_{20}H_{17}NH_3$ are used in these aspects of the invention. In another aspect of the present invention, therapeutically effective carborane derivatives are embedded within the liposome bilayer for subsequent administration. The resulting liposomes have heightened tumor selectivity and can be used as an encapsulation vehicle for the previously mentioned borane derivatives and for other drugs. In yet another aspect of the present invention novel derivatized boranes are developed for use in boron neutron capture therapy.

DETAILED DESCRIPTION OF THE PREFERRED EMBODIMENTS

Figure 1:
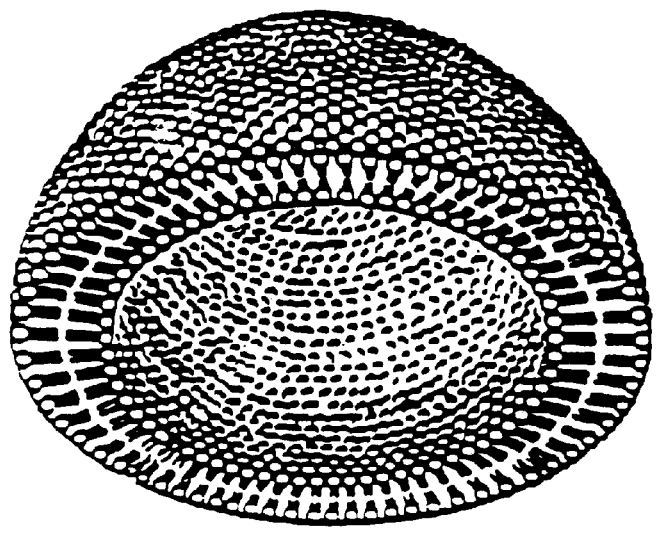
FIG. 1 is a drawing showing liposome membrane constituents and their structure.
Figure 1:
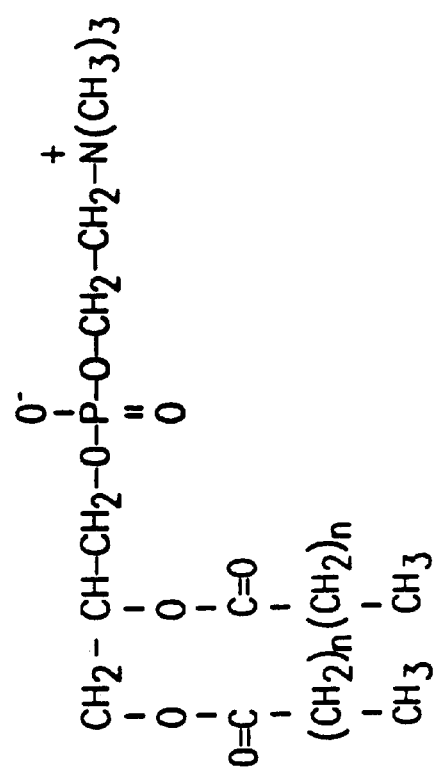
Figure 1:
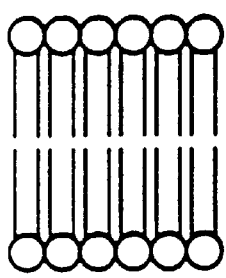

The following is a description of the preferred embodiments of the present invention including the best mode presently contemplated by the inventors.

"Vesicle" refers to a micelle which is in a generally spherical form, often obtained from a lipid which forms a bilayered membrane and is referred to as a "liposome". Liposomes are microscopic structures consisting in part of phospholipids. Methods for forming these liposomes are, by now, well known in the art and any such methods can be employed in the context of the present invention. See, e.g., U.S. Pat. No. 4,753,788 to Gamble and U.S. Pat. No. 4,935,171 to Braken. Typically, they are prepared from a phospholipid, for example, distearoyl phosphatidylcholine (also known as "DSPC"), and may include other materials such as neutral lipids, for example, cholesterol, and also surface modifiers such as positively or negatively charged compounds. Phospholipids are composed of two fatty acid chains condensed with glycerol with an additional substitution of a phosphate ester head group. By incorporating certain phospholipid molecules, a liposome is obtained which is stable in vivo. It is known that phase transition points are a function of hydrocarbon chain length, see Lanford, *The HydroDhobic Effect*, 2nd Ed. (1980). Certain phospholipid molecules exhibit phase transitions at relatively high temperatures (greater than 37° C.) and use of these phospholipids in compositions described herein provide liposomes with improved stability in vivo.

The stability of the DSPC micelles may be enhanced by the incorporation of cholesterol. Positively charged molecules such as stearylamine or aminomannose or aminomannitol derivatives of cholesterol or negatively charged molecules such as dialkyl phosphate may also be incorporated into the vesicles. [Certain carborane species, as discussed in detail below, may be incorporated into the vesicle's bilayer.]

When phospholipid micelles are introduced into the blood stream, the micelles move to the specific locations of cancerous growth in the patient's body. To enhance movement of the phospholipid vesicles to the specific locations, positively charged phospholipid vesicles may first be introduced into the patient's blood stream to block the macrophages or other phagocytic cells in the patient's body. The positively charged molecules bound to such phospholipid vesicles may be an aminomannose or aminomannitol derivative of cholesterol. Concurrently or after a suitable period of time such as approximately one (1) hour, other phospholipid vesicles may be introduced into the patient's blood stream to move to the specific locations in the body. Such phospholipid vesicles may include cholesterol and may be neutral or may be positively charged as by the inclusion of a stearylamine or aminomannose or aminomannitol derivative of cholesterol or may be negatively charged as by the inclusion of a dicetyl phosphate.

A wide variety of lipid particles may form delivery vesicles which are capable of the intact intracellular transport of the encapsulated contents. For example, other phospholipid delivery vehicles, such as disclosed in the Vestar, Inc. patent publication EP0272091 which is incorporated herein by reference, may be employed. These vehicles are composed of a single encapsulating phospholipid membrane associated with an amphiphile-associated substrate. However, the lipid particles are preferably comprised of phospholipids and most preferably are liposomes.

As noted above, either as multilamellar or unilamellar vesicles, liposomes have proven valuable as vehicles for drug delivery in animals and in humans. Active drugs, including small hydrophilic molecules and polypeptides, can be trapped in the aqueous core of the liposome, while hydrophobic substances can be dissolved in the liposome bilayer membrane. The liposome structure can be readily injected and can form the basis for both sustained release and drug delivery to specific cell types, or parts of the body. Multilamellars, primarily because they are relatively large, are usually rapidly taken up by the reticuloendothelial system (the liver and spleen). The invention typically utilizes vesicles which remain in the circulatory system for hours and break down after internalization by the target cell. For these requirements, the tumor lt treating agents of the present invention preferably utilize unilamellars having a diameter of less than 250 nm, and more preferably less than 100 nm.

With reference to FIG. 1, when hydrated, phospholipids form into bilayer structures with their fatty acid hydrocarbon tails pointed inward and the polar head groups outward. See K. Shelly, D. A. Feakes, M. F. Hawthorne, P. G. Schmidt, T. A. Krisch, W. F. Bauer, Proc. Natl. Acad. Sci. USA, 1992, 89 9039, which is incorporated herein by reference. The membrane bilayers in these structures typically encapsulate an aqueous volume, and form a permeability barrier between the encapsulated volume and the exterior solution. A hydrated phospholipid suspension, when agitated, forms multilamellar vesicles (MLV) like tiny onions, with water separating many bilayers in an onion-like form having diameters of 1–10 μm (1000–10,000 nm). Application of a shearing or homogenizing force such as sonication to an MLV suspension produces small unilamellar vesicles of a size range generally 30–250 nm and preferably 50 to 100 nm in average diameter. Unilamellar is generally meant to include from one to three, and preferably one, bilayer. The diameter of the liposome encapsulated borane tumor treating agents of the present invention is related to sonication time as well as the method by which the liposome is prepared.

The range of 50 to 100 nm is considered to be preferable from the standpoint of maximal circulation time in vivo and greater tumor specificity. In addition, if the liposomes are too large, the liver and the spleen take up too much of the encapsulated borane tumor treating agent. The actual equilibrium diameter is largely determined by the nature of the phospholipid used and the extent of incorporation of other lipids such as cholesterol.

Liposomes which have been applied to boron neutron capture therapy can carry hydrophilic salts of polyhedral borane anions of the present invention as solutes in the aqueous internal space of the vesicle. As discussed below, liposomes of the type employed for boron delivery are capable of excellent localization in a variety of tumors following intravenous injection.

Other lipids may be combined with phospholipids to produce liposomes having particular properties. Specifically, sterols such as cholesterol help stabilize the bilayer towards leakage and destruction in blood plasma. A stable liposome may be obtained by incorporating 5–50% cholesterol by weight of phospholipid into the liposome. Charged lipids or lipids with specific ligand functions may also be included. For example, although the liposome shown in FIG. 1 is comprised of a phospholipid having no net charge on its polar terminus, liposomes with net negative or positive charges can be prepared by techniques well known to those in the art. Small unilamellar vesicles comprised of from 3:1 to 1:1 mole ratio and preferably 1:1 mole ratio DSPC and cholesterol are particularly advantageous for delivery of the borane compounds of the present invention to tumors.

Boron compounds to be used in neutron capture therapy according to the present invention can have two or more atoms of boron per molecule, but preferably contain at least 10 and more preferably 20 atoms of boron per molecule. The isotopic content of the boron can range from natural abundance 19.78% $^{10}B$ to greater than 95% $^{10}B$ for a highly enriched compound. Natural abundance material is useful for test studies for encapsulation, biodistribution, stability and the like. Highly enriched material is advantageous for therapy where the maximum practicable concentration of $^{10}B$ is required.

Boron containing compounds useful for treating tumors according to one aspect of the present invention are highly water soluble, have small or no charge at physiological pH, are relatively impermeable to phospholipid bilayers of liposomes, and are not toxic or have low toxicity to the therapy subject. Examples of such boranes, both free and liposome encapsulated, include those of the formula $X_yB_{20}H_{17}L$. X is selected from the group consisting of alkali metals and tetra alkyl ammonium. Preferably X is Na, K, Cs or Rb, and alkyl includes methyl, ethyl and other alkyls which do not render the resulting salt insoluble. L is any 2 electron donor and y is 1 to 4. Preferably L is selected from the group consisting of —$NHR_1R_2$ wherein $R_1$ and $R_2$ are the same or different and are selected from the group consisting of hydrogen, benzyl, alkyl and diamine (e.g., ethylene diamine); —$SR^1R_2$ wherein $R_1$ and $R_2$ are the same or different and are selected from the group consisting of H or alkyl; —CN; —CO; —NCO; —$CH_2OH$; —$CO_2R_1$; —alkyl; —$NHCONHR_1$; —COOH and —$CONHR^1$, where $R_1$ is selected from the group consisting of hydrogen, benzyl, alkyl and diamine. More preferably, L is selected from the group consisting of —$NH_3$, —Ph—$CH_2$—$NH_2$, —$NH_2CH_2CH_2NH_2$ and —$NH_2(CH_2)_7CH_3$. Optimally, L is —$NH_3$.

Liposome encapsulated tumor treating agents of the present invention include a unilamellar liposome where the liposome has at least one encapsulating bilayer and an internal space defined by the encapsulating bilayer. A borane compound is encapsulated within the internal space. The borane compound is selected from the group consisting of $X_yB_{20}H_{17}L$ as described above and $X_sB_{10}H_9L$, wherein X and L are defined as above and s is 1 or 2. Most preferably, the encapsulated borane is selected from the group consisting of $Na_yB_{20}H_{17}NH_3$ where y is 1 or 3, and $Na_2B_{10}H_9NCO$.

A borane concentration inside the liposome of at least 100 mM, preferably 150 mM to 400 mM and more preferably 200 mM to 250 mM, minimizes osmotic pressure while maximizing boron content inside of the liposome, is necessary for a boron compound having at least 10 boron atoms per molecule. Of course, with a lower amount of boron atoms per molecule, a higher concentration is required. The resulting liposome solution is stable to leakage of the material inside, such that less than 10% of the boron material leaks out over a period of 3.5 months.

The present invention extends to methods of performing boron neutron capture therapy (BNCT) by administering the free boranes and the borane-containing liposomes discussed above and thereafter, subjecting the patient to a source that emits neutrons. Such a source is described, for example, in U.S. Pat. No. 4,516,535 to Russell, Jr.

Liposome encapsulated borane compounds are prepared by probe sonication of the dried film preferably composed of equimolar amounts of the phospholipid and cholesterol with the hydrating solution (typically 5 ml, 250–300 mM of the borane containing salt). The hydrated lipid samples can be sonicated using a Sonics & Materials "Vibracell" probe sonicator with a microtip operated at the maximum power setting for the microtip. The solution is maintained at 65° C. under a nitrogen atmosphere and sonicated for about 15–30 minutes. The sample is then allowed to cool to room temperature to produce small unilamellar vesicles whose average diameter is preferably less than 250 nm and more preferably 50–100 nm.

The vesicles can be separated from the remaining free borane salt by eluting on a column of Sephadex G-25-80 (medium) with isotonic phosphate-buffered saline or lactose at an osmolarity approximately equal to physiological. Liposomal separations can then be diluted with the appropriate buffer to a lipid concentration of 23–24 mg/ml and sterilized by filtration through a 0.22 μm Millipore membrane. The integrity of the encapsulated boron salt can be confirmed by $^{11}B$ NMR at 160 MHz.

The size of the liposomes can be determined by dynamic light scattering using methods known to those versed in the art. The encapsulated concentration of boron can be gaged by measuring the total borane concentration in each sample and then in the effluent after ultrafiltration to correct for material outside the liposomes. The concentration of boron can be determined by inductively coupled plasma atomic emission spectroscopy (ICP-AES).

The therapeutic effectiveness of the borane agents of the present invention can be characterized by biodistribution murine studies. All murine biodistribution studies utilized female BALB/c mice (16–20 g), with EMT6 tumors implanted in the right flank 7–10 days prior to the experiment. Tumor mass at the time of sacrifice was 125–350 mg. Injections of liposome emulsions (200 μl) were made in the tail vein. Prior to sacrifice, each mouse was anesthetized with halothane and bled into heparinized syringes via cardiac puncture. The blood was then placed into tared cryogenic tubes. While under anesthesia, the mice were euthanized via cervical dislocation. The tumor, liver, and spleen were dissected and also placed in tared cryogenic tubes. Blood and tissues were stored frozen until analyzed.

Biodistributions are plotted as boron concentration in micrograms of boron per gram of tissue on the Y axis and time in hours on the X axis. In general, four tissues are analyzed: tumor and blood because of their therapeutic interest, and liver and spleen because these tissues are known to competitively bind liposomes in vivo.

Figure 2A:
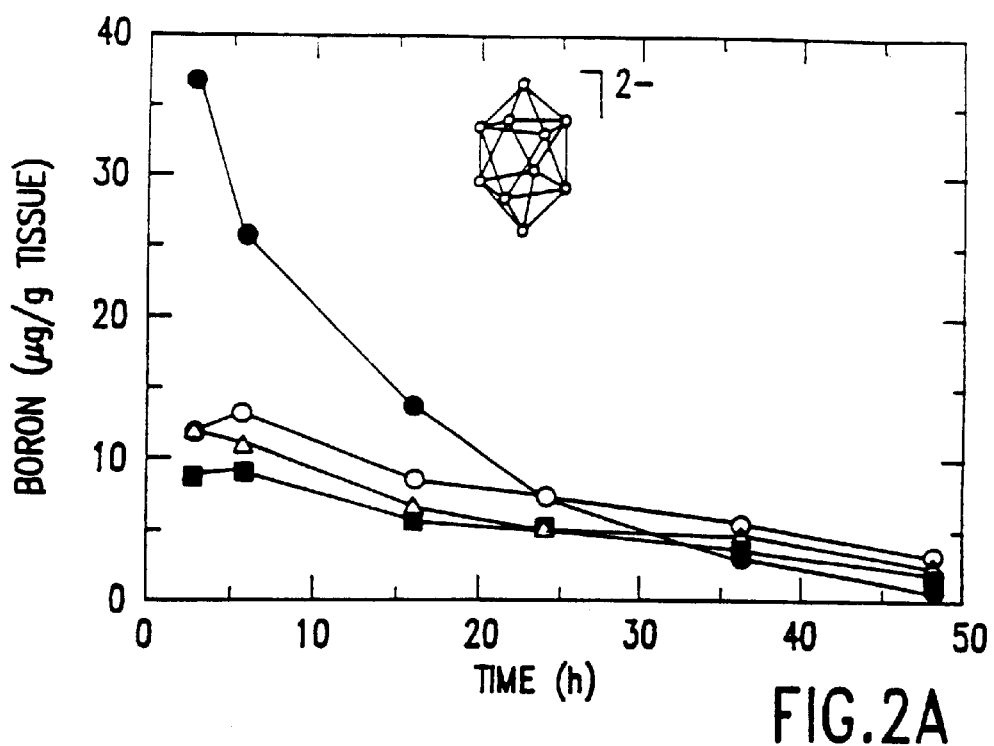
FIG. 2 shows biodistributions of $Na_2B_{10}H_{10}$ and $Na_2B_{12}H_{11}SH$ in BALB/c mice bearing EMT6 tumors.
Figure 2B:
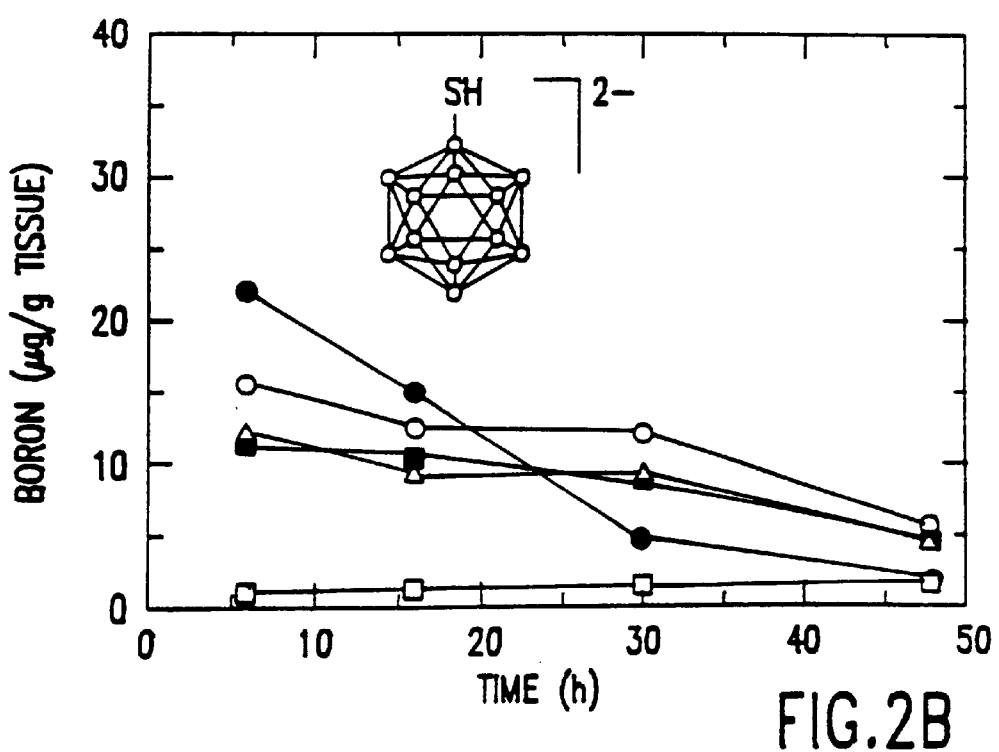

FIG. 2 shows the biodistributions of $Na_2B_{10}H_{10}$ and $Na_2B_{12}H_{11}SH$ in BALB/c mice bearing EMT6 tumors. This figure shows that both of these compounds are non-therapeutic as the concentration of the boron active in the tumor is initially fairly low and drops off rather rapidly.

Figure 3:
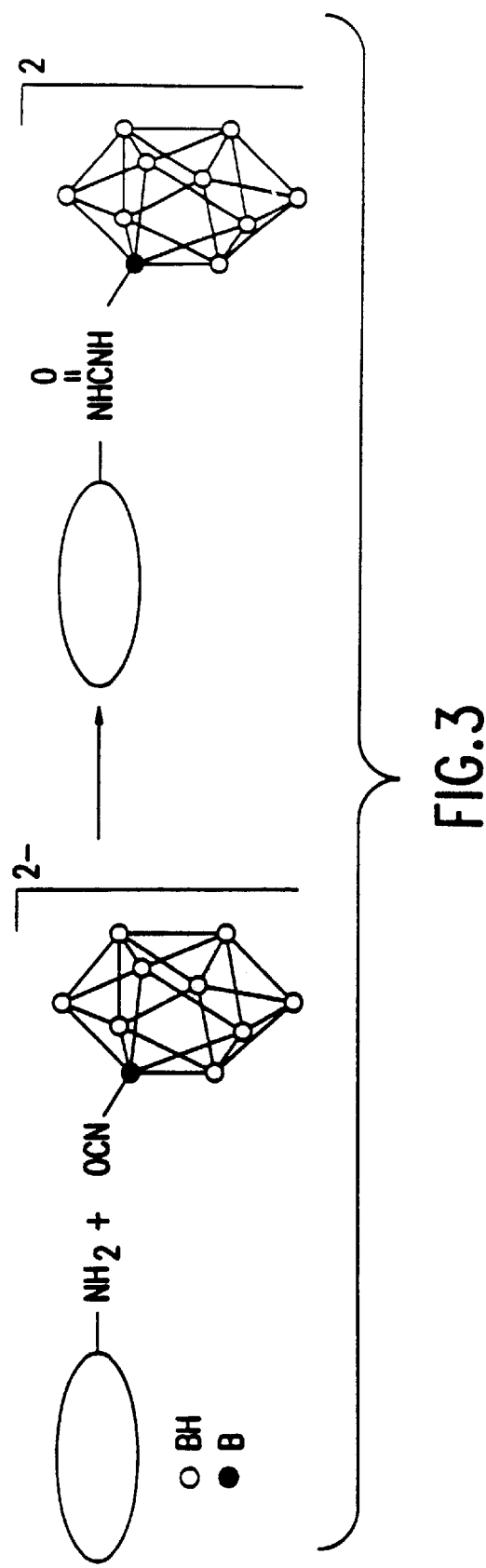
FIG. 3 is a proposed reaction of $B_{10}H_9NO^{2-}$ with intracellular protein.

It is believed that the borane compounds of the present invention including those which are derivatives of $B_{10}H_{10}{}^{2-}$ are more reactive than the prior art $Na_2B_{10}H_{10}$ because of intracellular protein binding. Thus, the present invention includes a method of treating tumors including the step of administering a borane compound which is capable of being nucleophilically attacked by an intracellular protein in vivo and subjecting the tumor to thermal neutrons. See FIG. 3 which shows the reaction of $B_{10}H_9NCO^{2-}$ with intracellular protein.

Figure 4A:
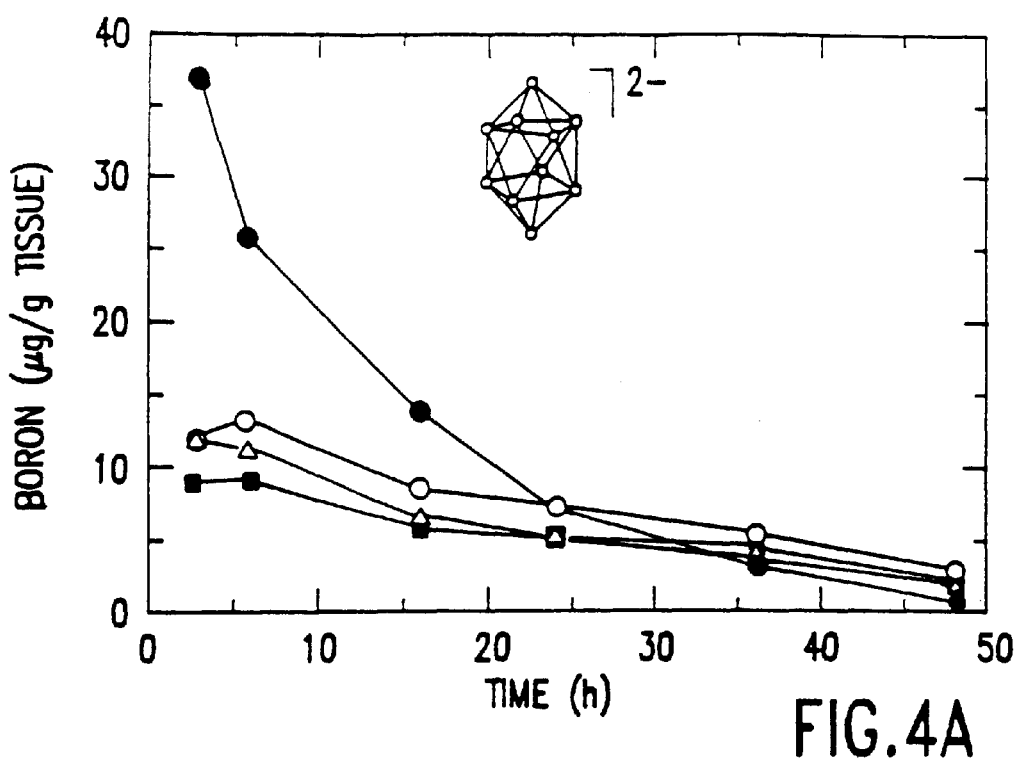
FIG. 4 shows the biodistributions of $Na_2B_{10}H_{10}$ and $Na_2B_{10}HgNCO$ in BALB/c mice bearing EMT6 tumors.
Figure 4B:
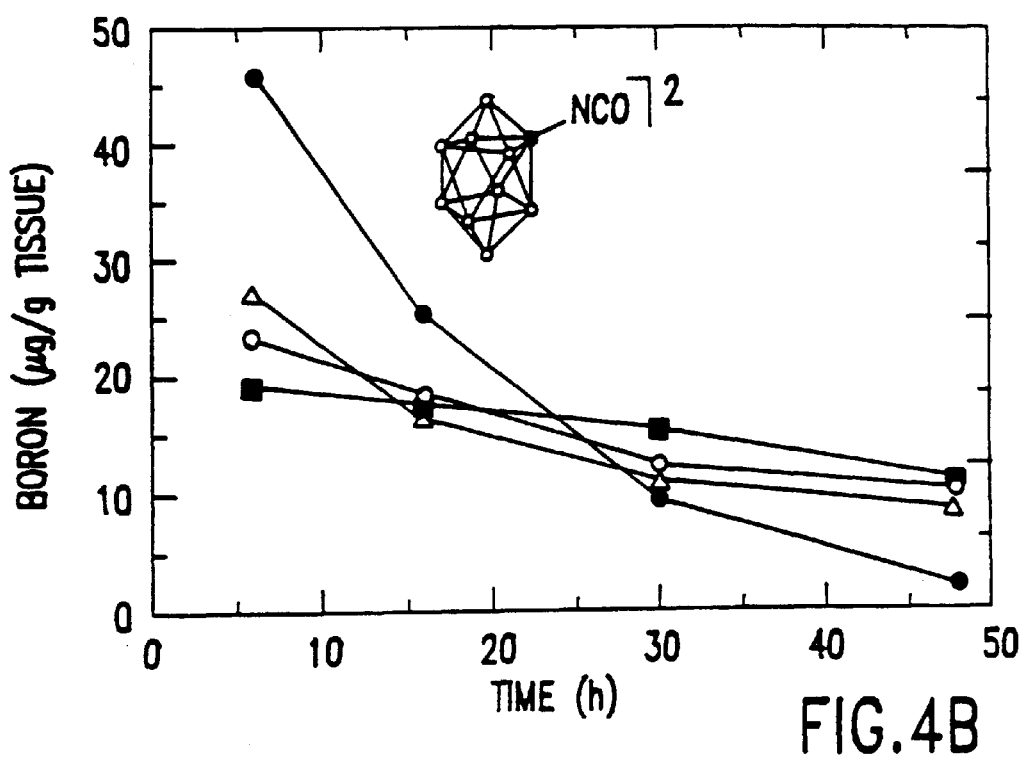

With reference to FIG. 4, one can readily see that the liposomal $Na_2B_{10}H_9NCO$ derivative is far superior than the parent $Na_2B_{10}H_{10}$ moiety. The tumor uptake with $Na_2B_{10}H_{10}$ begins at 10 µg/g; whereas, the liposomal $Na_2B_{10}H_9NCO$ begins around 20. Thus, with the latter moiety, the tumor is taking up more boron by a factor of 2. Also, the drop off is not as rapid and therefore adding the NCO functional group makes the boron agent more active. The $B_{10}H_{10}{}^{2-}$ ion demonstrated a biodistribution characterized by a rapid clearance of the boron compound from all tissues, including the tumor.

The biodistribution of $B_{10}H_9NCO^{2-}$ demonstrated an initial tumor boron concentration of approximately 20 micrograms boron per gram of tissue. This concentration remains relatively stable over a 30 hour time period.

Figure 5:
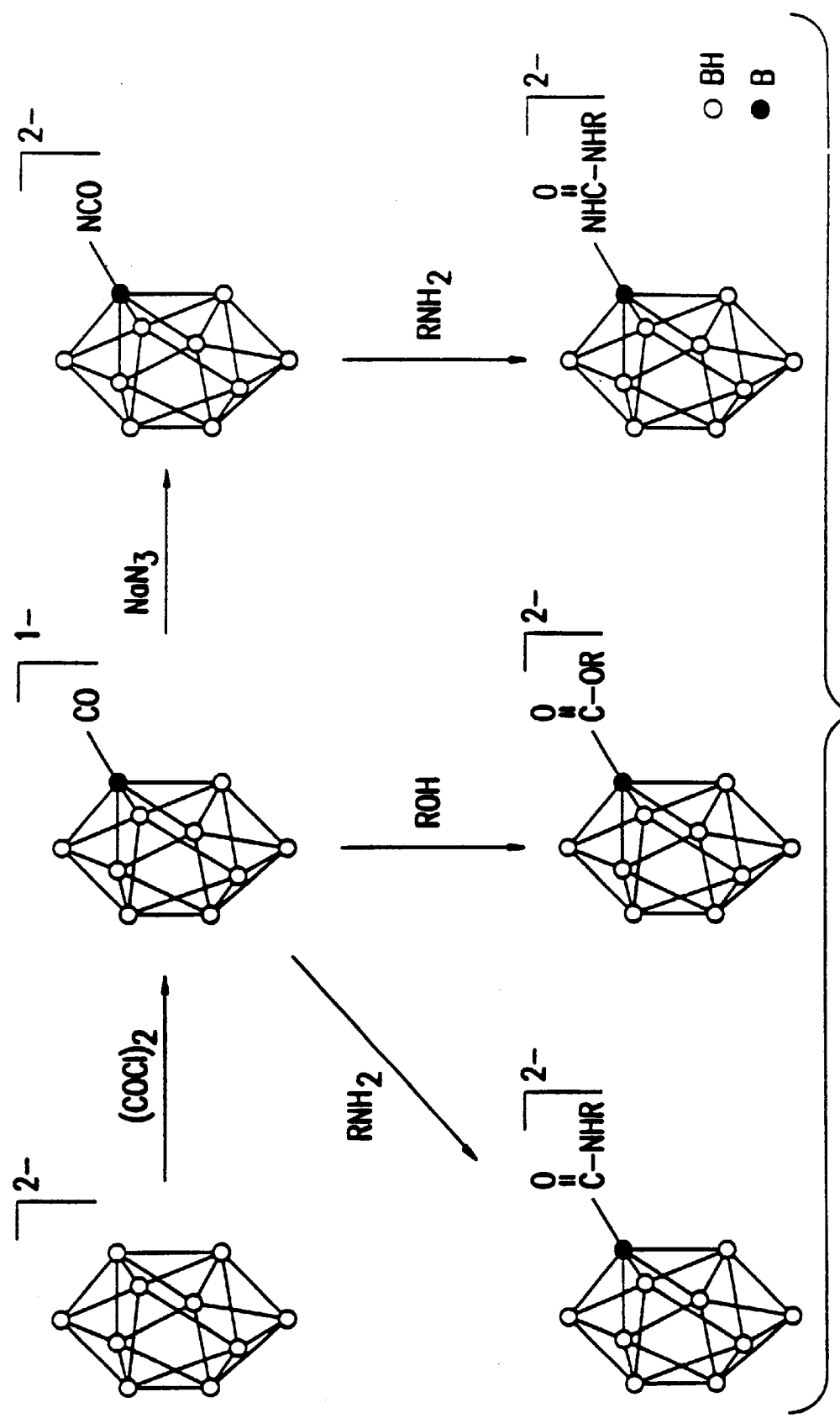
FIG. 5 shows a variety of boron agents capable of intracellular binding which are derivatives of $B_{10}B_{10}^{2-}$.

A schematic of certain preferable of the $B_{10}H_{10}{}^{2-}$ derivatives according to the present invention is shown in FIG. 5. The preparation of these derivatives is generally described in Shelly, Hawthorne, and Knobler, Inorg. Chem. 31, 2889 (1992), which is hereby incorporated by reference.

The $XB_{10}H_9L$ species of the present invention can be prepared from $[2\text{-}B_{10}H_9CO]^{1-}$ which itself is prepared by a novel reaction which is another aspect of the present invention. It has been found that the reaction of oxalyl chloride $(COCl)_2$ with $[B_{10}H_{10}]^{2-}$ proceeds rapidly and essentially quantitatively at room temperature with the evolution of carbon monoxide to produce the carbonyl derivative $[2\text{-}B_{10}H_9CO]^-$ shown in Scheme I below. Preferably, the $B_{10}H_{10}{}^{2-}$ may take the form of $[Ph_3PMe]B_{10}H_{10}$.

Scheme 1
Transformations of the $B_{10}H_9CO^-$ ion.

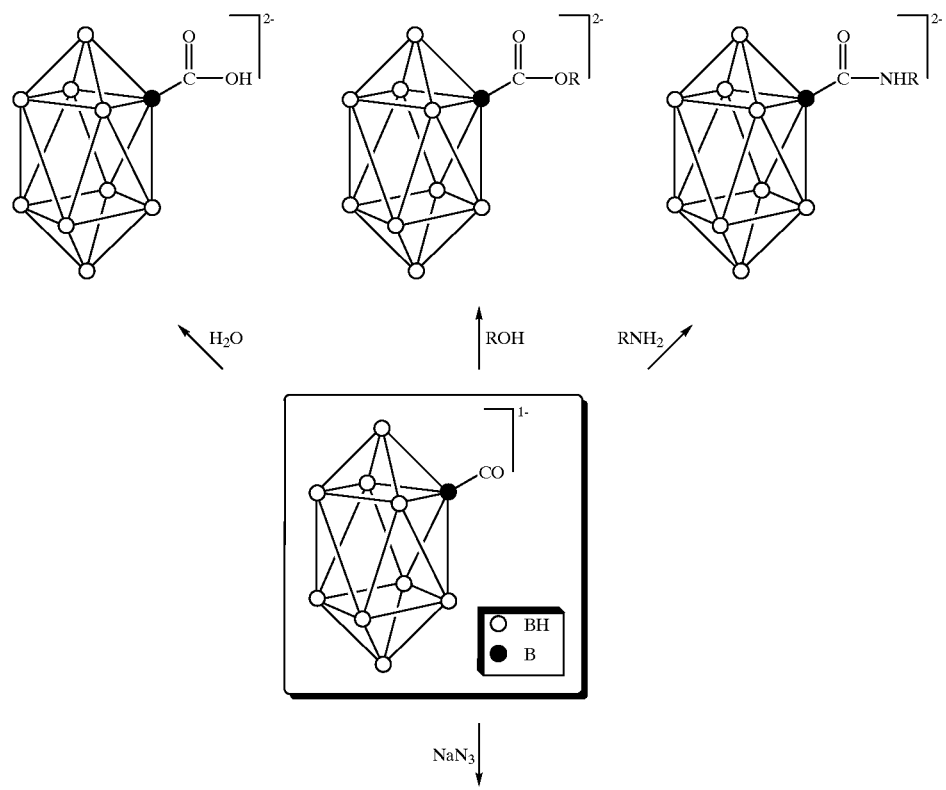

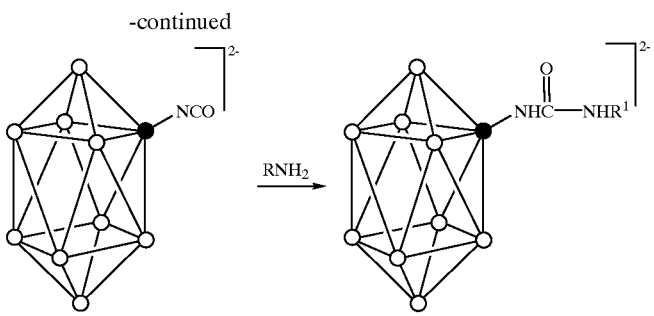

The cleanest reaction is observed employing [Ph$_3$PMe] [B$_{10}$H$_{10}$] in CH$_2$Cl$_2$, but the reaction can be used with several salts of [B$_{10}$H$_{10}$]$^{2-}$ including preferably cesium, tetramethylammonium and triethylammonium and with other solvents such as acetonitrile and tetrahydrofuiran. The reaction product exhibits a strong infrared peak at 2129 cm$^{-1}$. The $^{11}$B{$^1$H} spectrum of the reaction mnixture in CH$_2$Cl$_2$ exhibits seven signals, consistent with equatorial substitution, and shows only traces of by-products. The substituted boron is indicated by a high field resonance at −43.8 ppm (relative to BF$_3$.Et$_2$O) which is a singlet in the proton coupled spectrwn. [Ph$_3$PMe][2-B$_{10}$H$_9$CO] may be isolated as alight tan solid in 85% yield, or the reaction mixture may be used directly infirher reactions. The structure of [2-B$_{10}$H$_9$CO]$^-$ has been determined by X-ray crystallography and shows a linear B-C-O array with a C-O distance of 1.13 A.

The utility of the [2-B$_{10}$H$_9$CO]$^-$ anion results from its ease of conversion to a variety of other species usefuil for BNCT as depicted Scheme I above and FIG. 5. Although [2-B$_{10}$H$_9$CO]$^-$ is relatively insensitive to moisture in the solid state or in solution, it is easily hydrated in aqueous solvent mixtures to form [2-B$_{10}$H$_9$CO$_2$H$^{2-}$. [Ph$_3$PMe]$_2$[2-B$_{10}$H$_9$CO$_2$H] been confirmed by crystallographic analysis.

The reaction of [2-B$_{10}$H$_9$CO]$^-$ with an amine (RNH$_2$) results in the formation of an amide ([2-B$_{10}$H$_9$CONHR]$^{2-}$) as long as an excess of the amine is present to absorb the acid formed by the reaction. R is a lipophilic alkyl, preferably selected from the group consisting of ethyl, propyl and hexyl. Esters are produced by the combination of [2-B$_{10}$H$_9$CO]$^-$ with alcohols; in this case, the reaction is slow or incomplete unless an auxiliary base such as triethylamine is added to absorb the acid formed.

A very useful transformation of [2-B$_{10}$H$_9$CO]$^-$ occurs from its reaction with azide ion in acetonitrile. The carbonyl undergoes a Curtius-type rearrangement to form the isocyanate [2-B$_{10}$H$_9$NCO]$^{2-}$ indicated by an infrared absorption at 2304 cm$^{-1}$. This ion, whose structure has been determined by X-ray crystallography, is stable in neutral aqueous solution but is rapidly hydrolyzed in acidic media. The [2-B$_{10}$H$_9$CO]$^-$ ion therefore offers a high-yield route to the production of many boron-rich species for boron neutron capture therapy. Detailed protocols of preparing certain of these species is as follows:

[Ph$_3$PMe][closo-2-B$_{10}$H$_9$CO] ([Ph$_3$PMe]•1) A mixture of [Ph$_3$PMe]$_2$[closo-B$_{10}$H$_{10}$] (6.73 g, mmol), which is readily available from (Et$_3$NH)$_2$B$_{10}$H$_{10}$, in 125 mL of dry CH$_2$Cl$_2$ was chilled in an ice bath with stirring. A solution of (COCl)$_2$ in CH$_2$Cl$_2$ (5.1 mL, 10.2 mmol) was added via syringe, and the mixture was stirred at 0° C. for 30 min. The solution as allowed to warm to room temperature and stirred an additional 30 min. The volume of the solution was reduced to ~15 mL by mechanical vacuum. The resulting solution was passed through a 2.5×30 cm column of silica gel, eluting with CH$_2$Cl$_2$, and the effluent was evaporated in vacuo. The residue was recrystallized from CH$_2$Cl$_2$/Et$_2$O to yield 3.59 g (8.5 mmol, 85%) of light tan [Ph$_3$PMe$_3$]•1. Anal. Calcd for C$_{20}$H$_{27}$B$_{10}$OP: C, 56.85; H, 6.44; B, 25.59. Found: C, 57.01;H, 6.30; B, 25.50. IR (cm$^{-1}$, KBr disk): 2519 (s), 2501 (s), 2129 (s). $^{11}$B{$^1$H} NMR (ppm, CH$_2$Cl$_2$, relative areas in parentheses): 6.4 (1), 6.0 (1), −17.9 (1), −25.9 (2), −28.4 (2) −43.8 (1). The −43.8 ppm resonance was a singlet in the proton-coupled spectrum.

[Ph$_3$PMe]$_2$[closo-2-B$_{10}$H$_9$CO$_2$H] ([Ph$_3$PMe]$_2$•2). A mixture of [Ph$_3$PMe]$_2$closo-2B$_{10}$H$_{10}$] (5.52 g, 8.2 mmol) in 100 mL of CH$_2$Cl$_2$ was allowed to react with 4.2 mL of (COCl)$_2$ as described above. After vacuum removal of the solvent, the residue was dissolved in 200 mL of hot acetone, and the solution was stirred with 3 g of activated charcoal. The mixture was filtered, and 150 mL water was added to the filtrate. The solution was neutralized by addition of 0.5 N NaOH, and acetone was allowed to evaporate from the mixture at room temperature. The resulting crystals were filtered off and dried to give 4.21 g of [Ph$_3$PMe]$_2$•2 (5.9 mmol, 72%). Anal. Calcd for C$_{39}$H$_{46}$B$_{10}$O$_2$P$_2$: C, 65.35; H, 6.47; B, 15.08. Found: C, 65.18; H, 6.43;B, 15.20. IR (cm$^-$, KBr disk): 2458 (s), 1694 (m), 1256 (m). $^{11}$B{$^1$H} NMR (ppm, CH$_2$Cl$_2$, relative areas in parentheses): −0.5 (1), −1.3 (1), −25.5 (1), −28.6 (3), −29.6 (4).

[Et$_3$NH]2[closo-2-B$_{10}$H$_9$NCO] ([Et$_3$NH]$_2$•3). A solution of [Et$_3$NH]$_2$[closo-2-B$_{10}$H$_{10}$] (3.22 g, 10 mmol) in 150 mL of MeCN was allowed to react with 5 mL of (COCl)$_2$ as described above. Solid NaN$_3$ (1.4 g, 21 mmol) was added, and the mixture was stirred overnight. The mixture was then filtered, 200 mL ether was added, and the solution was chilled to −20° C. overnight. The precipitate was filtered off and dried under vacuum, yielding 2.73 g of [Et$_3$NH]$_2$•3 (7.5 mmol, 75%). Analytical and crystallographic samples of [Et$_3$NH]$_2$•3 were purified fuirther by recrystallization from acetone/pentane. Anal. Calcd for C$_{13}$H$_{41}$B$_{10}$N$_3$O: C., 42.94; H, 11.37; N, 11.56;B,29.73. Found: C, 42.81; H, 11.18; N, 11.71;B,29.50. IR (cm$^{-1}$, KBr disk): 2538 (s), 2505 (s), 2475 (s), 1013 (m), 967 (m), 597 (w), 577 (w). $^{11}$B{$^1$H} NMR (ppm, MeCN, relative areas in parentheses): −2.3 (2), −16.8 (1), −25.2 (2), −25.6 (2), −28.3 (2, −31.6 (1). The resonance at −16.8 ppm was a singlet in the proton-coupled spectrum.

The synthesis of [B$_{10}$H$_9$CO]$^-$ is described above. The synthesis may also be performed starting with: Cs$_2$[B$_{10}$H$_{10}$], [Et$_3$NH]$_2$[B$_{10}$H$_{10}$], [(CH$_3$)$_4$N]$_2$[B$_{10}$H$_{10}$], or [Ph$_3$PCH$_3$]$_2$[B$_{10}$] in acetonitrile; or [Et$_3$NH]$_2$[B$_{10}$H$_{10}$]; [(CH$_3$)$_4$N]$_2$[B$_{10}$B$_{10}$], or [Ph$_3$PCH$_3$]$_2$[B$_{10}$H$_{10}$] in methylene chloride. The synthesis of [B$_{10}$H$_9$NCO]$^{2-}$ may be performed with any of the above cations but has been found to proceed smoothly only in acetonitrile.

To synthesize [B$_{10}$H$_9$CO$_2$C$_2$H$_5$]$^{2-}$ and [B$_{10}$H$_9$CO$_2$CH$_3$]$^{2-}$, [Et$_3$NH][B$_{10}$H$_9$CO] (2.5 mmol) was stirred in 50 ml of the appropriate alcohol in the presence of 0.5 mL $Et_3N$ for 30 minutes. The alcohol was removed in vacuo and the residue was recrystallized from acetonitrile/ether. $[Et_3NH]_2$ $[B_{10}H_9CO_2C_2H_5]$ (in acetonitrile) $^{11}B\{^1H\}$ 0.8, −0.4, −23.4, −27.2; $[Et_3NH]_2[B_{10}H_9CO_2CH_3]$ (in acetonitrile) $^{11}B\{^1H\}$ 0.8, −0.4, −23.9, −27.5.

To synthesize $[B_{10}H_9CONHC_3H_7]^{2-}$, $[Et_3NH]$ $[B_{10}H_9CO]$ (2.5 mmol) was stirred in 50 mL of propylamine for 30 minutes. The propylamine was removed in vacuo and the residue was dissolved in ethanol containing $[(CH_3)_4N]Cl$ and precipitated with ether. $[(CH_3)_4N]_2[B_{10}H_9CONHC_3H_7]$ (in acetonitrile) $^{11}B\{^1H\}$ 0.3, −24.7, −26.7, −27.3.

Figure 6B:
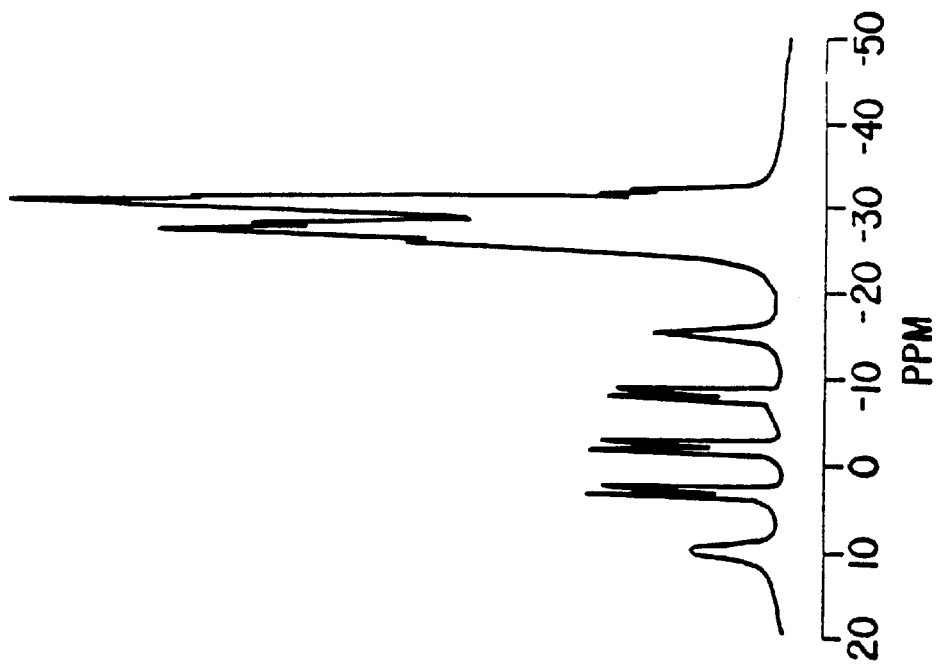
FIG. 6 shows the X-ray crystal structure and $^{11}B$ NMR of the tetramethyl ammonium salt of $B_{20}H_{17}NH_3^{3-}$.
Figure 6A:
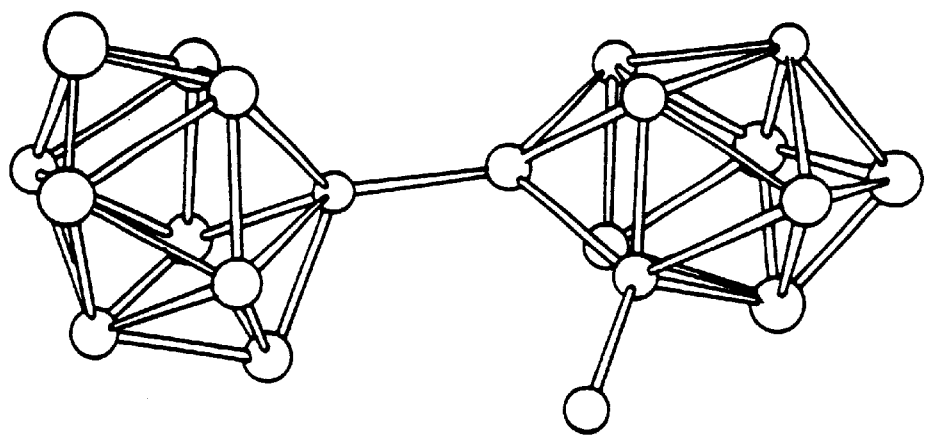

As discussed above, one aspect of the present invention is the use in BNCT of borane moieties capable of undergoing nucleophilic attack. Such compounds possess the ability to react with intracellular protein moieties. For example, the $B_{10}H_{10}{}^{2-}$ anion is known to undergo oxidative coupling to produce the $B_{20}H_{18}{}^{2-}$ species. Compounds capable of intracellular binding include derivatives of the monocarbonyl substituted $B_{10}H_{10}{}^{2-}$ ion discussed above, substituted derivatives of $B_{20}H_{18}{}^{2-}$, such as an amine derivative discussed below, reduced $B_{20}H_{18}{}^{2-}$ derivatives, which may be oxidized intracellularly to produce the corresponding reactive $B_{20}H_{18}{}^{2-}$ derivative, carbonyl substituted (acylium ion analogs), of $B_{10}H_{10}{}^{2-}$ and $B_{20}H_{18}{}^{4-}$ capable of protein $NH_2$ reactions. Salts of $B_{20}H_{17}NH_3{}^{3-}$ have been shown to be particularly useful for BNCT, both free and encapsulated by liposomes. FIG. 6 shows the tetramethyl ammonium salt of $B_{20}H_{17}NH_3{}^{3-}$.

To prepare another salt of $B_{20}H_{17}NH_3{}^{3-}$, $Na_3B_{20}H_{17}NH_3$, approximately 175 mL of liquid ammonia is condensed in a flask containing 3 mmol of dry $Na_2(n-B_{20}H_{18})$ and cooled by both a dry ice/acetone bath and condenser. An 18% suspension of sodium acetylide in xylene/light mineral oil (2.0 mL, 8 mmol of $NaC_2H$) is added dropwise via syringe. The dry ice/acetone bath is removed from the base of the reaction flask and the condenser is maintained for 3 hours. The ammonia is allowed to evaporate under a nitrogen atmosphere. The remaining solvent is removed in vacuo. Absolute ethanol (50 mL) is added and the resulting solution filtered. The product is precipitated using a saturated solution of $(CH_3)_4NCl$ in absolute ethanol. The solid is filtered and recrystallized from water/ethanol in 70% yield. The cation is exchanged to Na using standard methods. 160 MHz $^{11}B$ NMR ($CHCl_3$, δ referenced to external $BF_3 \cdot OEt_2$): 9.4 (s, 1 B), 3.0 (d, 1 B), −1.4 (d, 1 B), −7.1 (d, 1 B), −14.9 (s, 1 B), −24.8 (d), −26.2 (d), −29.0 (d) −31.0 (d).

Figure 7:
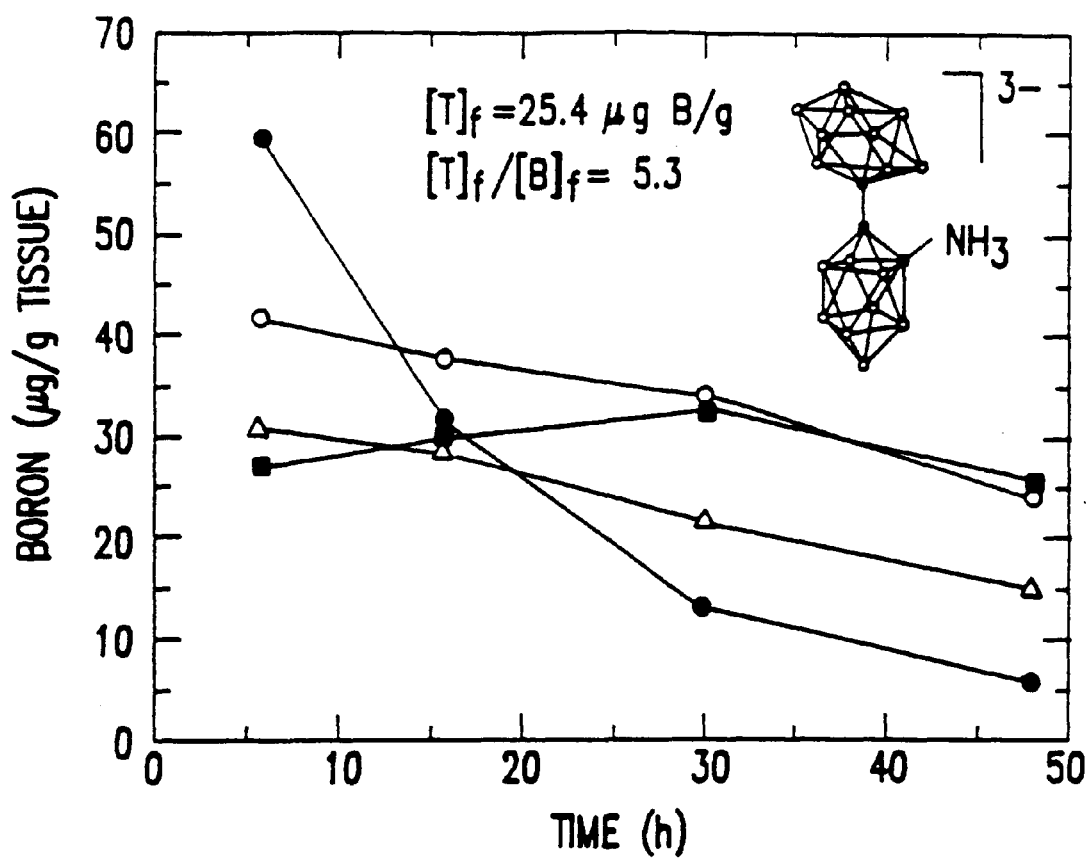
FIG. 7 shows the biodistribution of liposomal $Na_3B_{20}H_{17}NH_3$ in BALB/c mice bearing EMT6 tumors.

FIG. 7 shows the biodistribution characterization of $Na_3B_{20}H_{17}NH_3$ encapsulated in the 1:1 DSPC/cholesterol liposome discussed above in BALB/c mice bearing EMT6 tumors. Quite significantly, the tumor boron concentration increases over a period of approximately 30 hours and then slowly decreases, resulting in a final tumor boron concentration which is still 94% of the initial tumor boron concentration. All other tissues clear steadily over the 40 hour time period. The low blood boron concentration at 48 hours yields a tumor to blood boron ratio of 5.3. The final tumor boron concentration of 25.4 micrograms boron per gram tissue is approximately equal to the initial tumor boron concentration and is well within therapeutic levels. It is believed that the species $B_{20}H_{17}NH_3{}^{3-}$ is oxidized within the cell according to the following Scheme 2 and the resulting ion is very reactive to nucleophiles, for example, the terminal amine groups in the tumor cell. The single negative charge of the resulting $B_{20}H_{17}NH_3{}^-$ gives this species enhanced electrophilicity compared to $B_{20}H_{18}{}^{2-}$ ions and improved intracellular bonding.

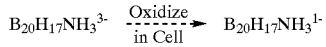

Scheme 2

Figure 8:
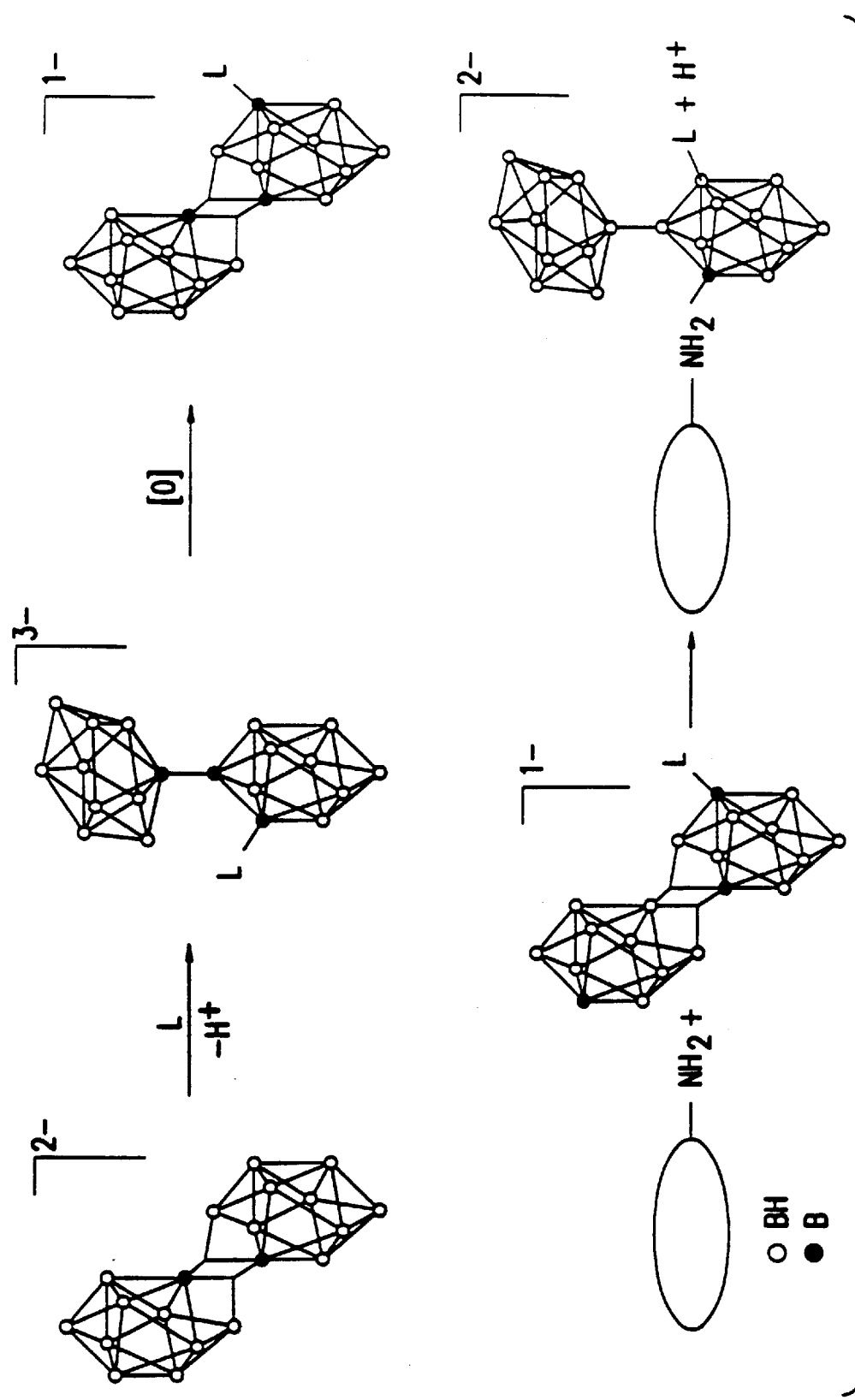
FIG. 8 shows the intracellular oxidation reaction and the subsequent nucleophilic attack by intracellular proteins.

In general, in addition to $NH_3$, other reduced, substituted $B_{20}H_{18}{}^{2-}$ derivatives are believed to be subject to intracellular oxidation after liposomal delivery according to Scheme 2. As shown in FIG. 8, the $B_{20}H_{17}L^{1-}$ species is particularly reactive with nucleophiles, e.g., intracellular proteins in tumor cells. Thus, the present invention includes the more reactive borane compounds $X_yB_{20}H_{17}L$ as discussed above and the corresponding liposome encapsulated compounds where y is 1 to 4. Methods of preparing certain of the $X_yB_{20}H_{17}L$ derivatives are as follows:

The amine derivatives of $[B_{20}H_{18}]^{2-}$, $[B_{20}H_{17}NH_2R]^{3-}$, are synthesized in the f manner:

Dry $Na_2[n-B_{20}H_{18}]$ (3 mmol) is dissolved in the desired amine (30 mL) under and atmosphere of nitrogen. Sodium acetylide, $NaC_2H$ (2.0 mL, 18% in a suspension of xylene/light mineral oil) is added to the solution via syringe. The mixture is allowed to stir for approximately one day at room temperature. The amine is removed in vacuo and absolute ethanol (50 mL) is added to the residue. The product is precipitated as the tetramethylammonium salt by the addition of a saturated solution of $(CH_3)_4NCl$ in absolute ethanol. Recrystallization of the precipitate from water/ethanol affords the desired product in approximately 70% yield. Benzylamine, $(B_{20}H_{17}NH_2CH_2C_6H_5)^{3-}$: $^{11}B\{^1H\}$ 10.0, 2.7, −2.0, −8.2, −13.0, −26.7, −29.6; Octylamine, $(B_{20}H_{17}NH_2(CH_2)_7CH_3)^{3-}$: $^{11}B\{^1H\}$ 9.0, 3.0, −1.0, −6.5, −12.5, −25.9, −28.8; and Ethylenediamine, $(B_{20}H_{17}NH_2CH_2CH_2NH_2)^{3-}$: $^{11}B\{^1H\}$ 9.0, 2.8, −0.9, 2.8, −0.9, −3.9, −6.3, −12.4, −28.1.

To prepare the oxidized amine species $[B_{20}H_{17}NH_3]^{1-}$, to a solution of 0.7 g of $[(CH_3)_4N][B_{20}H_{17}NH_3]$ in 40 mL distilled water at 0° C. was added slowly 20 mL of a 0.35 M ferric chloride solution ($FeCl_3 \cdot 6H_2O$). The reaction mixture was stirred for approximately one day. The product, which precipitated from solution, was filtered and dried.

To synthesize $[B_{20}H_{17}CN]^{4-}$, $[Et_3NH]_2[n-B_{20}H_{18}]$ (0.54 g, 1.2 mmol) was dissolved in 15 mL distilled acetonitrile. While under a nitrogen atmosphere, 0.86 g (5.5 mmol) $Et_4NCN$ was added. The solution was refluxed for approximately 24 hours. Cyano derivative, $[B_{20}H_{17}CN]^{4-}$: $^{11}B\{^1H\}$ 10.4, 0.8, −2.5, −4.5, −12.9, −23.2, −26.2, −27.1.

To synthesize $[B_{20}H_{17}SH]^{4-}$, dry $Na_2[n-B_{20}H_{18}]$ (2.5 mmol) is dissolved in a combination of distilled acetonitrile (50 mL) and distilled ether (20 mL). The solution is transferred via cannula to a flask containing anhydrous NaSH (0.31 g, 5.5 mmol). The solution is refluxed for approximately one week. The solvent was then removed in vacuo. Absolute ethanol (50 mL) was added which precipitated the product as the tetramethylammonium salt by adding a saturated solution of $(CH_3)_4NCl$ in absolute ethanol. Thiol derivative, $[B_{20}H_{17}SH]^{4-}$: $^{11}B\{^1H\}$ 4.1, 1.6, −0.7, −23.2, −24.6, −27.2.

Figure 9:
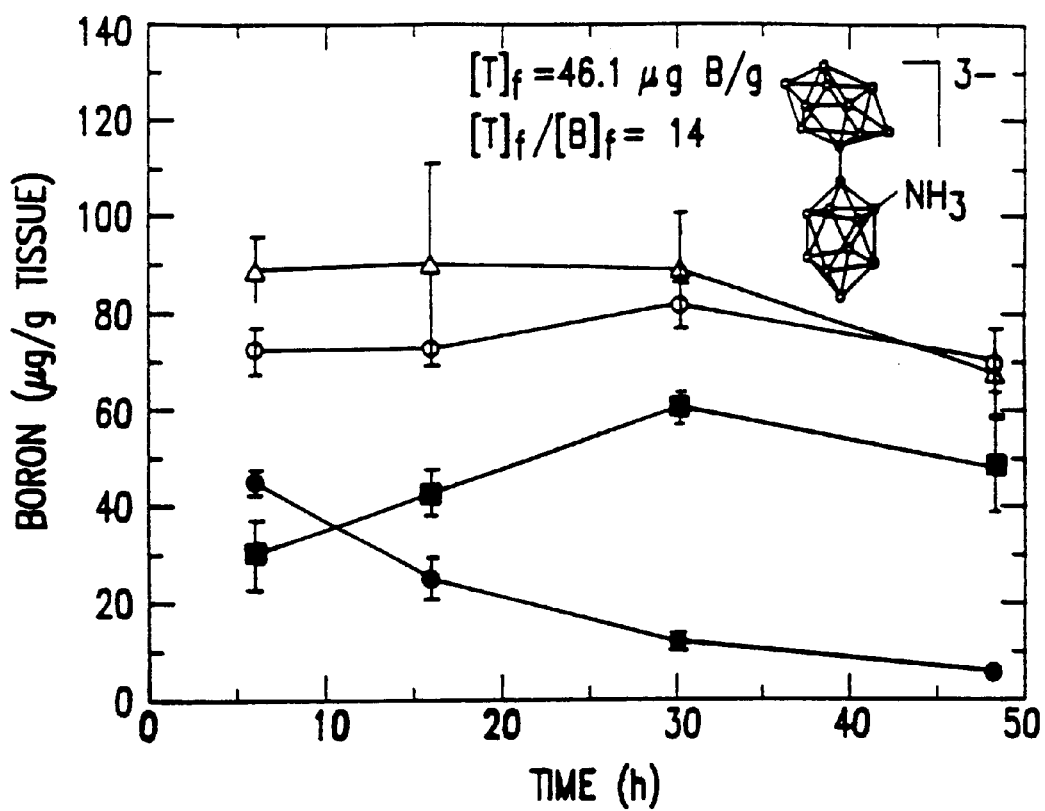
FIG. 9 shows another biodistribution of liposomal $Na_3B_{20}H_{17}NH_3$ in BALB/c mice bearing EMT6 tumors.

The previous example and FIG. 7 involved the encapsulation of $Na_3B_{20}H_{17}NH_3$ in a liposome having an approximately 110 nm average diameter. It has also been found that larger liposomes having active borane compounds encapsulated therein, or perhaps aggregates of similar liposomes, having a mean diameter of from 100 to 200 and preferably less than 250 nm also show therapeutic value. Reference here is made to FIG. 9 where the boron concentration in the tumor begins at 30 µg/g and increases over time to 60 µg/g.

Reference to therapeutic or therapeutic value or therapeutic amount or concentration is meant to refer to that amount of the borane species when disposed within a tumor cell and exposed to thermal neutrons results in the killing of tumor cells. This concentration range assumes use of 95% enriched $^{10}$B. If natural abundance or lower percentage enriched $^{10}$B is used, a higher concentration will be required as can be determined by routine experimentation.

Figure 10:
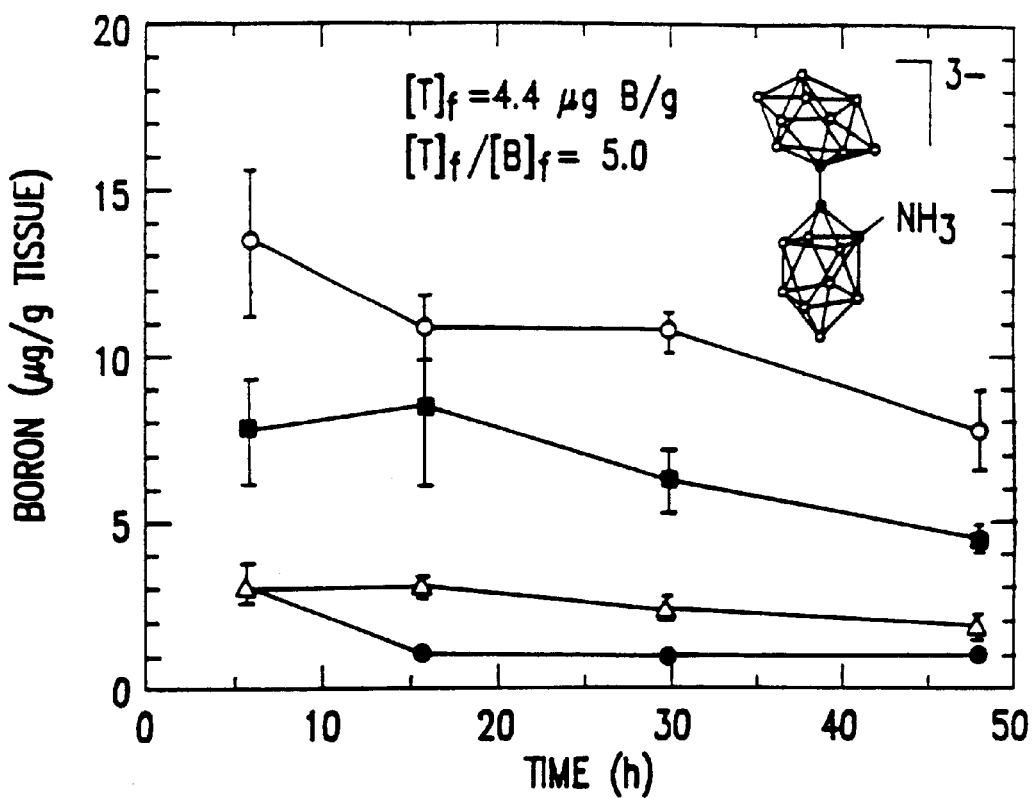
FIG. 10 shows the biodistribution of free $Na_3B_{20}H_{17}NH_3$ in BALB/c mice bearing EMT6 tumors.

In another aspect of the present invention, it has been found that free $Na_3B_{20}H_{17}NH_3$ also shows enhanced boron activity and tumor specificity. By free, it is meant that this compound is not encapsulated in a liposome. It is simply present when administered in a buffer such as phosphate buffered lactose or saline, and administered by injection. As shown in FIG. 10, this compound may provide therapeutic delivery by infusion over a long period of time thereby allowing accumulation within the tumor. It should be appreciated, that in general, other prior art free boron derivatives injected at comparable doses have not shown initial accumulation above 2 ppm; whereas, as shown in FIG. 10, the initial distribution in the tumor is about 8 ppm.

Figure 11:
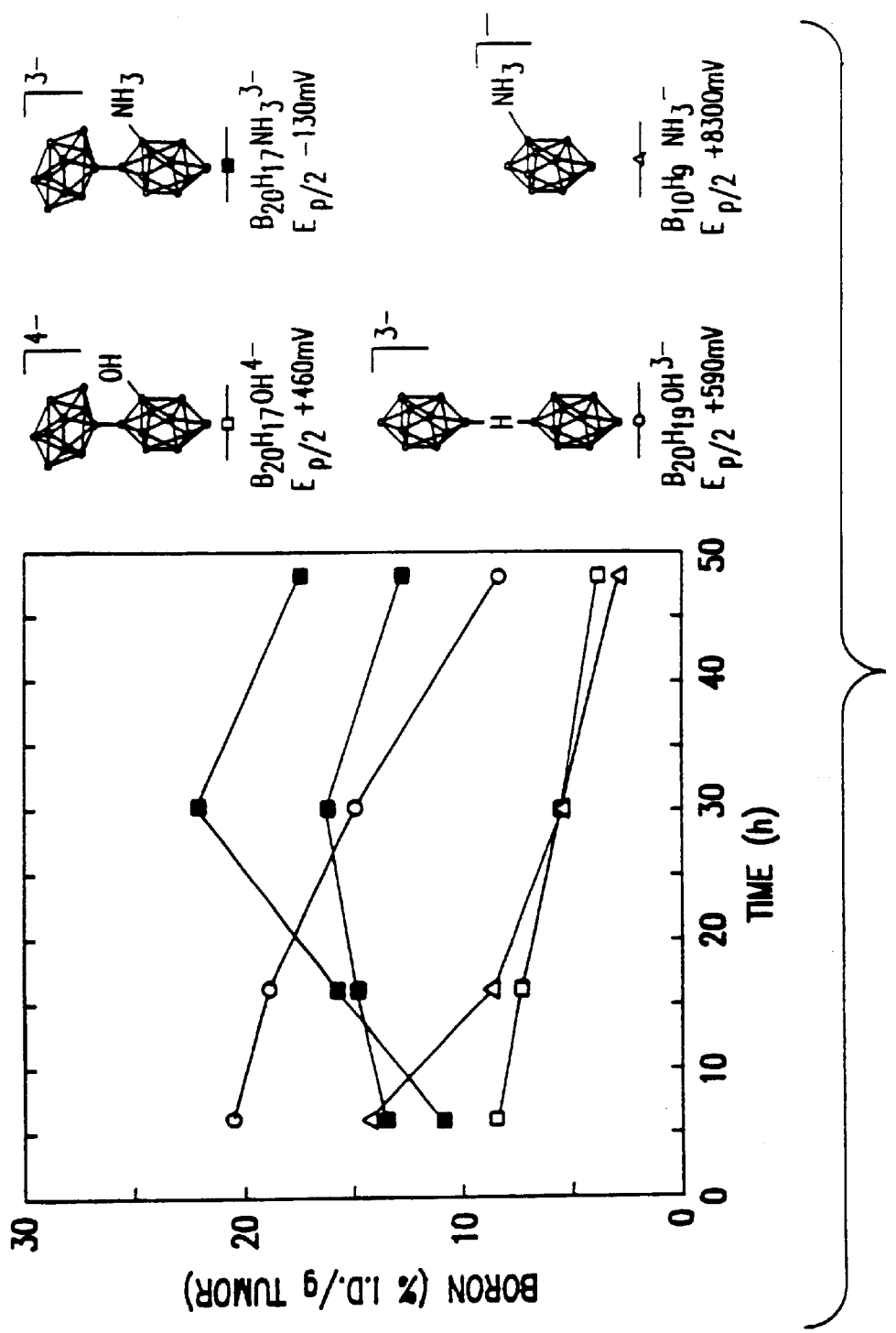
FIG. 11 shows the tumor boron retention of liposomal boranes in BALB/c mice bearing EMT6 tumors.

A comparison of the effectiveness of liposomal encapsulated boranes is shown in FIG. 11. The liposomal encapsulated boranes were prepared and the biodistribution measured as discussed above. It is shown that the $B_{20}H_{17}NH_3^{3-}$ species is far superior.

Another aspect of the present invention involves the embedment of lipophilic boron species in the phospholipid bilayer of the liposome. It is known that unilamellar liposomes of the type illustrated above as boron delivery vehicles preferentially deliver their contents to tumor cells in animals and humans in such a manner that tumor levels of effector molecules are 5–10 times that of normal tissue, including blood. According to this other aspect of the present invention it has been found that embedding certain carborane species into the liposome bilayer increases the tumor specificity of the liposome. By embedding the carborane tumor treating agents in the lipophilic bilayer membrane, the total amount of boron to be delivered by the liposome having a borane tumor treating agent encapsulated therein can also be increased.

This aspect of the present invention is directed to liposomes preferably unilamellar having at least one encapsulating bilayer and an internal space defined by the encapsulating bilayer where a carborane is embedded in the bilayer. This aspect of the present invention also involves the use of such carborane embedded liposomes for tumor treatment in BNCT, to increase the specificity of the liposome and to encapsulate therapeutic moieties such as the borane species discussed above and others known to those of skill in the art.

Liposomes with boron compounds embedded in the bilayer are prepared by hydrating the phospholipids in the presence of the boron compound to be embedded. Specifically, liposome emulsions were prepared by probe sonication of a dried film composed of a lipophilic boron species, in the desired amount, and equimolar amounts of the phospholipid and cholesterol with the hydrating solution (typically 250–300 mM in the boron-containing salt) at 65° C. for 15–30 minutes. The dried film is prepared by dissolving the lipophilic boron compound and the cholesterol:DSPC mixture in chloroform and removing the solvent in vacuo. The vesicles were homogenized by sonication and were separated from the remaining free borane salt by eluting through a column of Sephadex G-25 (medium) with isotonic phosphate-buffered saline or lactose. Liposomal preparations were diluted with the appropriate buffer to a lipid concentration of 25–30 mg/mL and sterilized by filtration through a 0.22 μm Millipore membrane.

The amount of boron embedded in the bilayer is ideally controlled by the amount of boron compound added to the DSPC:Cholesterol lipid mixture. Assuming the boron compound is not water soluble, all of the boron compound should be embedded, although this is not always the case. The quantity of boron embedded in a liposome is determined by ICP-AES analysis when no boron containing compound is encapsulated.

In general, to increase liposome specificity and for BNCT purposes, there is embedded in the bilayers preferably from 0.5 to 10 percent by weight and more preferably from 1 to 5 percent. Preferably, the bilayer comprises a phospholipid, such as DSPC and cholesterol, where the mole percent ratio of DSPC to cholesterol ranges from 1:1 to 3:1 and is preferably 1:1.

The carborane embedded within the liposome according to the present invention is generally selected from the group consisting of (a), (b), (c), (d), (e), (f) and (g) and mixtures thereof as follows:

(a)

A carborane of the formula:

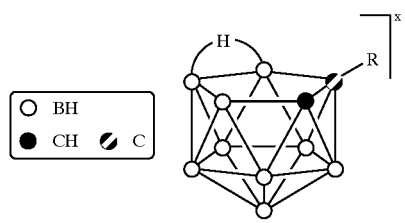

R is a lipophilic alkyl group, preferably $-(CH_2)_xCH_3$ where x ranges from 11 to 19, more preferably R is selected from n-$C_{16}H_{33}$ and n-$C_{18}H_{37}$. A long carbon chain, for example an R group of 16 carbon atoms, increases the stability of the bilayer because of the similarities between this compound and the phospholipid DSPC as evidenced by the polar head group and the long lipophilic side chains.

(b)

A carborane of the formula:

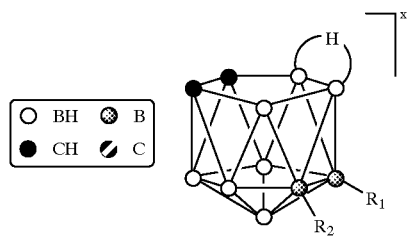

Figure 12:
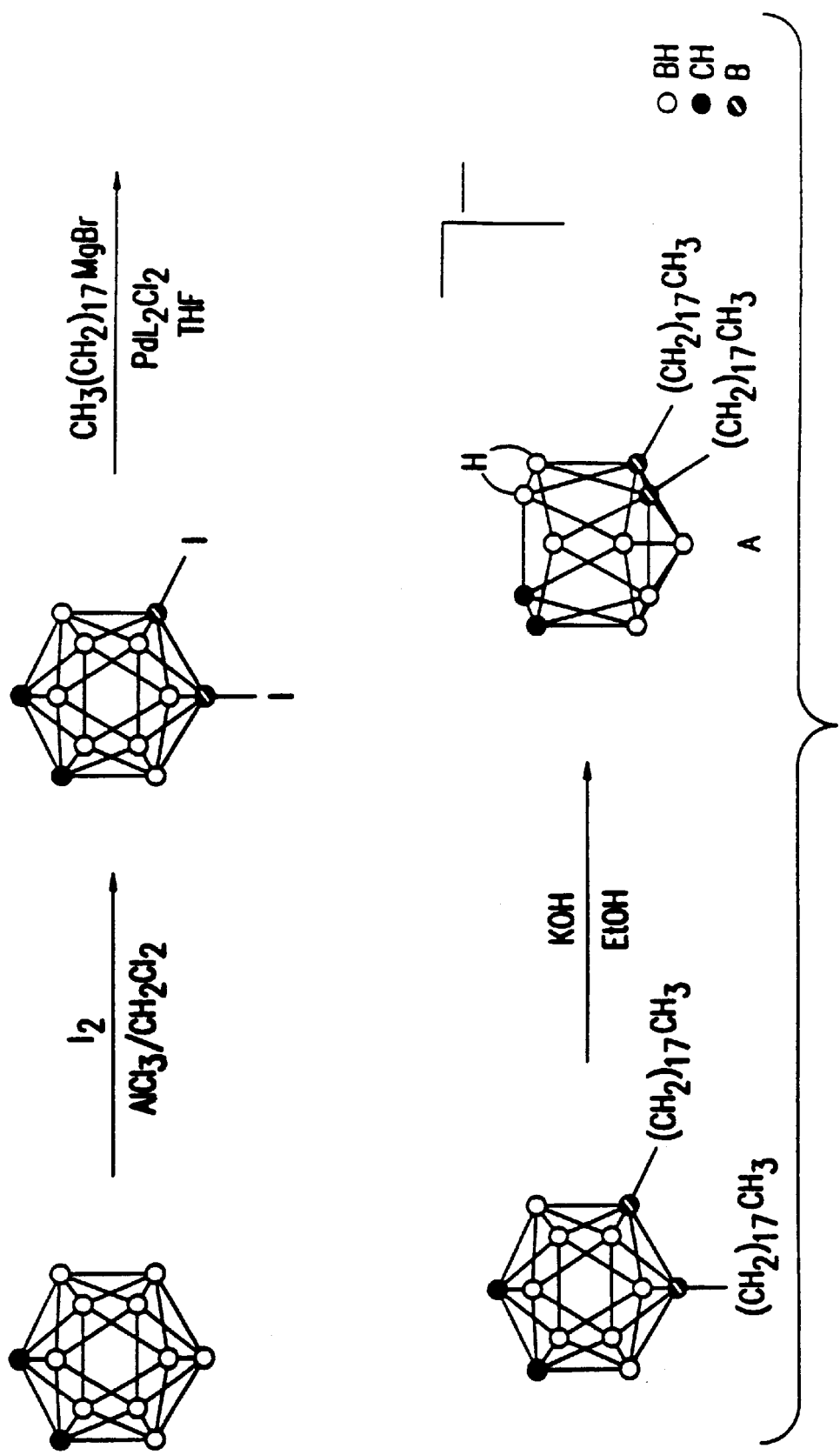
FIG. 12 shows the development of lipophilic boron species for phospholipid bilayer embedment.

With reference to FIG. 12, the double tailed carborane species A embeds in the bilayer better than the single tailed carborane species (a) discussed above.

The embedment of a boronated species characterized by a polar head group and two fatty acid tails as shown in FIG. 12 in the liposome bilayer stabilizes the bilayer membrane because it more closely mimics the structure of the phospholipid utilized. The synthesis of the two tailed compound is based on that described in Li, Ji.; Logan, C. F.; Jones, M. Jr.; *Inorg. Chem.* (1991), 30, 4866. Iodination of orthocarbonane followed by alkylation with a suitable Grignard reagent produces a dialkylated closo-carborane species. Degradation of this compound produces a species characterized by a polar head group, the nido-carborane, and two fatty acid tails, the two $C_{18}H_{37}$ chains.

(c)

A metallocarborane of the formula:

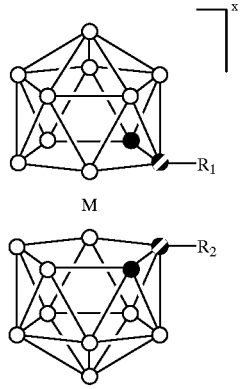

Figure 13:
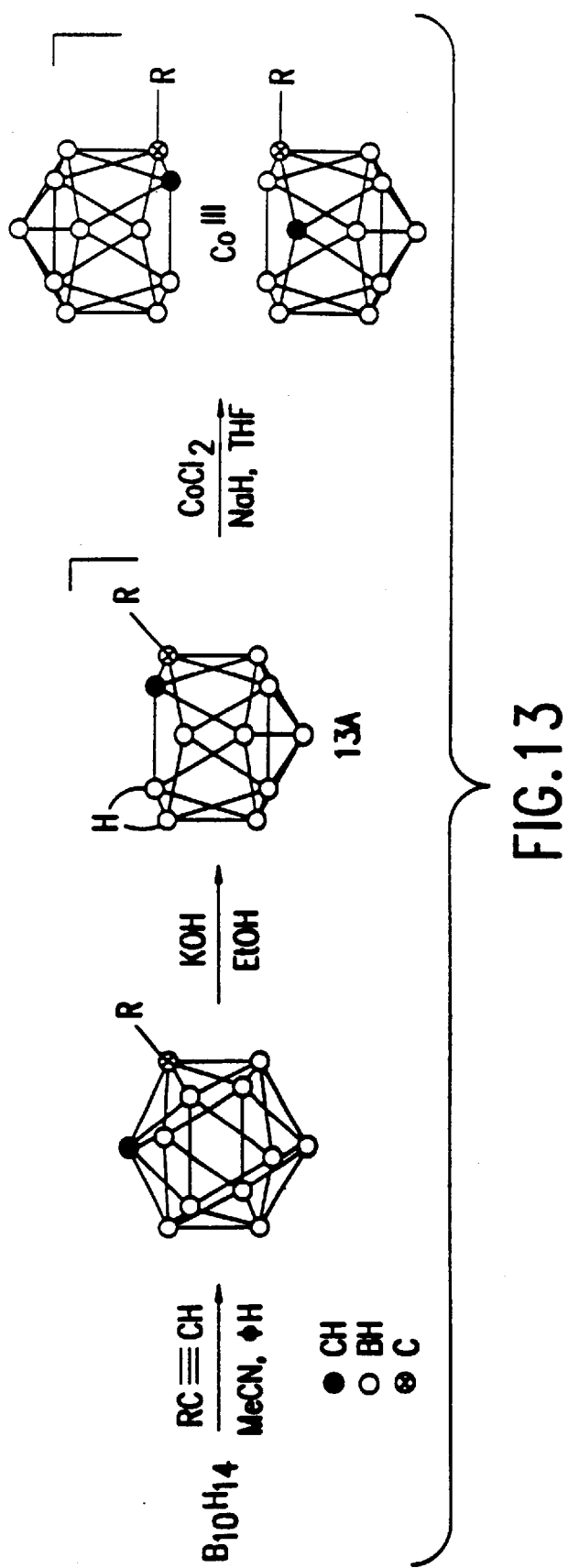
FIG. 13 shows the development of lipophilic boron species for phospholipid bilayer embedment.

M is a transition metal preferably selected from $Fe^{III}$, $Cr^{III}$ and $Co^{III}$. The cobalt derivative and its synthetic sequence is shown in FIG. 13.

(d)

A carborane of the formula:

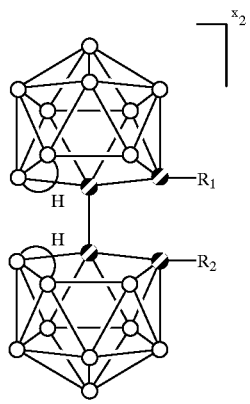

$R_1$ and $R_2$ for carborane species (b), (c) and (d) are the same or different and are selected from the lipophilic alkyl groups R discussed above with respect to carborane species (a), or $R_1$ or $R_2$ is H and the other of $R_1$ or $R_2$ is such a lipophilic alkyl group.

(e)

A carborane of the formula:

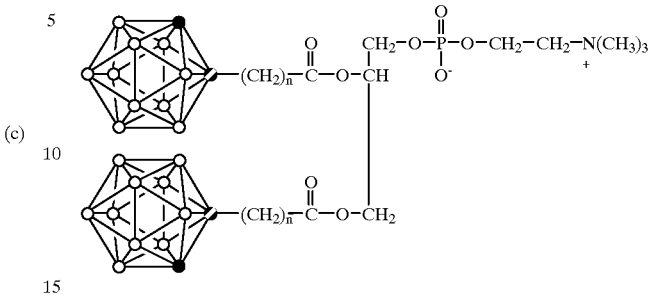

, where n is preferably 12, 14, 16 or 18.

The cation X for each of (a)–(e) is preferably selected from the group consisting of the alkali metals and tetra alkyl ammoniums discussed above with respect to $X_yB_{20}H_{17}L$.

(f)

A closo-carborane of the formula:

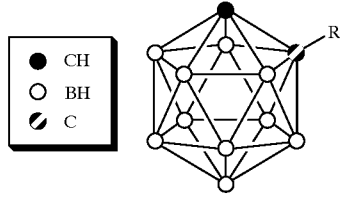

R is as defined above. This is prepared, for $R=n-C_{16}H_{33}$, as discussed below.

(g)

A closo-carborane of the formula:

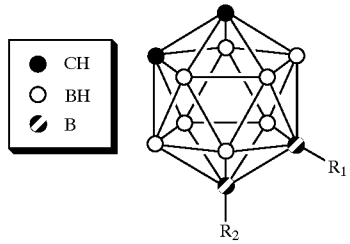

$R_1$ and $R_2$ are defined above, preferably —$(CH_2)_xCH_3$, where x ranges from 5 to 19. This is prepared for $R=n-C_{16}H_{33}$, as discussed below.

However, one skilled in the art will recognize that various other boranes can be used in place of the compounds set forth in (a) through (g) above. For example, the following compounds (where cation $M^+$ below and the cation X above in (a) through (e), are interchangeable) may also be used:

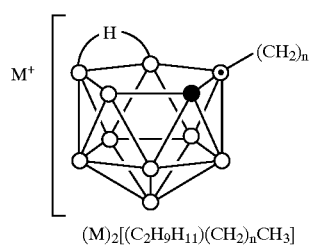
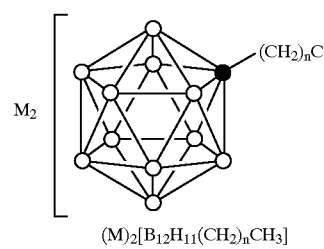
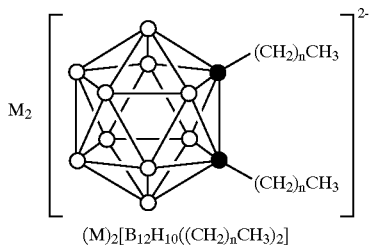

$(M)_2[(C_2H_9H_{11})(CH_2)_nCH_3]$    $(M)_2[B_{12}H_{11}(CH_2)_nCH_3]$    $(M)_2[B_{12}H_{10}((CH_2)_nCH_3)_2]$

○ = BH   $M^+$ = Na, K, $N(CH_3)_4$,
● = CH   $N(CH_2CH_3)_4$
⊙ = C    n = 13–17

○ = BH   $M^+$ = Na, K, $N(CH_3)_4$,
● = B    $N(CH_2CH_3)_4$
         n = 11–17

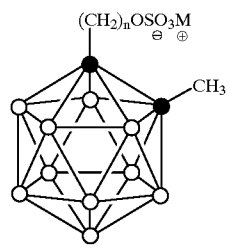
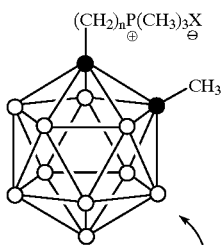
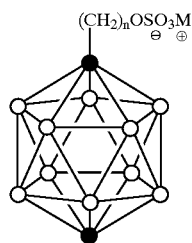
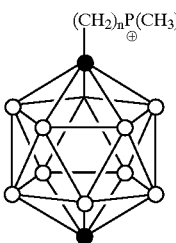

$(1\text{-}CH_3\text{-}2\text{-}(CH_2)_nOSO_3M)(1,2\text{-}C_2B_{10}H_{10})$ $(1\text{-}CH_3\text{-}2\text{-}(CH_2)_nP(CH_3)_3X)(1,2\text{-}C_2B_{10}H_{10})$ $(1,12\text{-}(CH_2)_nOSO_3M)_2(1,12\text{-}C_2B_{10}H_{10})$ $(1,12\text{-}(CH_2)_nP(CH_3)_3X)_2(1,12\text{-}C_2B_{10}H_{10})$ ○ = B    n = 11–17
         X = Cl, Br
● = C    M = alkali metal, tetraalkylammonium

[cf. claim 61]

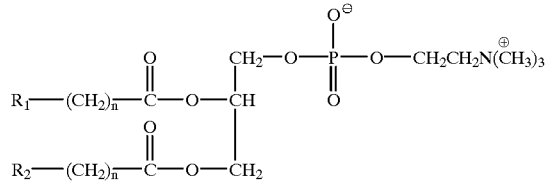
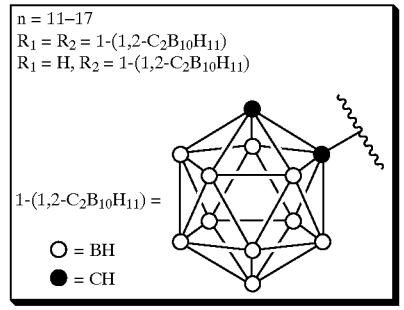

n = 11–17
$R_1 = R_2 = 1\text{-}(1,2\text{-}C_2B_{10}H_{11})$
$R_1 = H, R_2 = 1\text{-}(1,2\text{-}C_2B_{10}H_{11})$ $1\text{-}(1,2\text{-}C_2B_{10}H_{11})$ =

○ = BH
● = CH

As discussed above, the specificity of a unilamellar liposome can be increased by embedding a carborane within the liposome bilayer. Preferably the carborane is selected from species (a)–(g) above or mixtures thereof.

Protocols for preparing certain of these carborane species is as follows:

Preparation of the Dicarbollide Dianion, NaK-(3)-1,2-$B_9C_2H_{10}R$. A solution of 5.0 g (25.9 mmoles) of NaK-1,2-$B_9C_2H_{11}R$ which is readily available in 75 ml of tetrahydrofuran was added slowly to a stirring suspension of sodium hydride, 1.51 g (63 mmoles, 2.70 g of a 56% dispersion in mineral oil which had been washed twice with 30 ml of tetrahydrofuran), in 90 ml of the same solvent. The reaction mixture was stirred at reflux temperature under nitrogen for 3 hr. Stirring was then stopped and the reaction mixture allowed to cool to room temperature. When the excess sodium hydride had settled, the clear tetrahydrofuran solution of NaK-1,2-$C_2B_9H_{10}R$ was collected.

Preparation of the (3)-1,2-Dicarbollylcobalt (III) Derivatives, $Cs[(3)\text{-}1,2\text{-}B_9C_2H_{10}R]_2Co$. To a stirred suspension of 1.20 g (9.2 mmoles) of anhydrous cobaltous chloride in dry tetrahydrofuran (50 ml) was added under nitrogen a tetrahydrofuran solution of NaK-(3)-1,2-$B_9C_2H_{10}R$ (5.2 mmoles) which is readily available as noted above. The resulting black mixture was refluxed for 2 hr under nitrogen, cooled, and filtered to remove the cobalt metal and sodium chloride. After the removal of the solvent in vacuo, the residue was extracted with hot water, the resulting aqueous solution filtered, and the filtrate treated with cesium chloride.

To prepare 9,12-$[CH_3(CH_2)_{17}]_2$-1,2-$C_2B_{10}H_{10}$, a mixture of 2.31 g magnesium (95 mmol) and 31.7 g $CH_3(CH_2)_{17}Br$ was refluxed in 200 mL THF for 3 h. The Grignard reagent was slowly added to a suspension of 9,12-$C_2B_{10}H_{10}I_2$ (5.01 g, 12.7 mmol), $Pd[P(C_5H_5)_3]_2Cl_2$ (227 mg), and CuI (65 mg) in 50 mL THF at 0° C., and then brought to reflux for 90 h. After cooling the solvent was removed in vacuo. The residue was digested in 250 mL ether and washed with 50 mL water, 50 mL 1 N HCl, and 50 mL water. The ether solution was dried over magnesium sulfate and the solvent removed on a rotary evaporator. The crude product was purified by chromatography on silica, eluting with hexane, to yield 2.4 g 9,12-[CH$_3$(CH$_2$)$_{17}$]$_2$-1,2-C$_2$B$_{10}$H$_{10}$ (30%). 160 MHz $^{11}$B NMR (CHCl$_3$, δ referenced to external BF$_3$•OEt$_2$): 8.7 (s, 2 B), –8.8 (d, 4B), –14.8 (d, 4 B), –16.0 (d, 2 B).

To prepare K$^+$[5,6-[CH$_3$(CH$_2$)$_{17}$]$_2$-7,8-C$_2$B$_9$H$_{10}$]$^-$, 1.04 g 9,12-[CH$_3$(CH$_2$)$_{17}$]$_2$-1,2-C$_2$B$_{10}$H$_{10}$ (1.6 mnmol) was added to a solution of 1 g KOH in 60 mL ethanol and refluxed for 24 h. The solution was cooled, saturated with carbon dioxide, filtered, and the solvent was removed under vacuum. The residue was recrystallized from benzene to yield 1.02 g (94%) K$^+$[5,6-[CH$_3$(CH$_2$)$_{17}$]$_2$-7,8-C$_2$B$_9$H$_{10}$]$^-$. 160 MHz $^{11}$B NMR (CHCl$_3$, δ referenced to external BF$_3$•OEt$_2$): –5.0 (s, 2B), –11.6 (d, 2B), –18.9 (d, 1 B), –21.0 (d, 2 B), –29.5 (d, 1 B), –35.6 (d,1 B).

To prepare 1-CH$_3$(CH$_2$)$_{15}$-1,2-C$_2$B$_{10}$H$_{11}$, a mixture of 12.27 g B$_{10}$H$_{14}$ (100 mmol), 150 mL benzene, and 42 mL acetonitrile were refluxed overnight. Octadecyne (25.00 g, 100 mmol) was added dropwise to the refluxing solution and the solution refluxed an additional 36 hours. After cooling the solvent was removed in vacuo. Dissolved residue in 1:1 ether:pentane and extracted 5×100 mL with 1 N NaOH. The organic fraction was collected, dried over Mg$_2$SO$_4$, and the solvent removed on a rotary evaporator. The crude product was purified by chromatography on silica, eluting with pentane. The product was isolated in 30% yield. 160 MHz $^{11}$B NMR (pentane, δ referenced to external BF$_3$•OEt$_2$): –1.7 (d, 1 B), –5.1 (d, 1 B), –8.6 (d, 2 B), –10.7 (d, 2 B), –11.5 (d, 2 B), –12.4 (d, 2 B).

To prepare K$^+$[7-[CH$_3$(CH$_2$)$_{15}$]-7,8-C$_2$B$_9$H$_{10}$]$^-$, 5.19 g 1-CH$_3$(CH$_2$)$_{15}$-1,2-C$_2$B$_{11}$ (14 mmol) was added to a solution of 1.8 g KOH in 100 mL ethanol and refluxed for 24 h. The solution was cooled, saturated with carbon dioxide, filtered, and the solvent was removed under vacuum. The residue was extracted using benzene in a Soxhlet extraction apparatus and the product was isolated in 90% yield. 160 MHz $^{11}$B NMR (C$_6$H$_6$, δ referenced to external BF$_3$•OEt$_2$): –9.4 (d, 2 B), –12.4 (d, 1 B), –15.8 (d, 1 B), –16.5 (d, 2 B), –20.7 (d, 1 B), –31.7 (d, 1 B), –35.6 (d, 1 B).

With reference to FIG. 13, when the potassium carborane derivative species 13A is embedded in the bilayer, the resulting liposome is a negative liposome which leads to a more selective liposome and better biodistribution.

Figure 14:
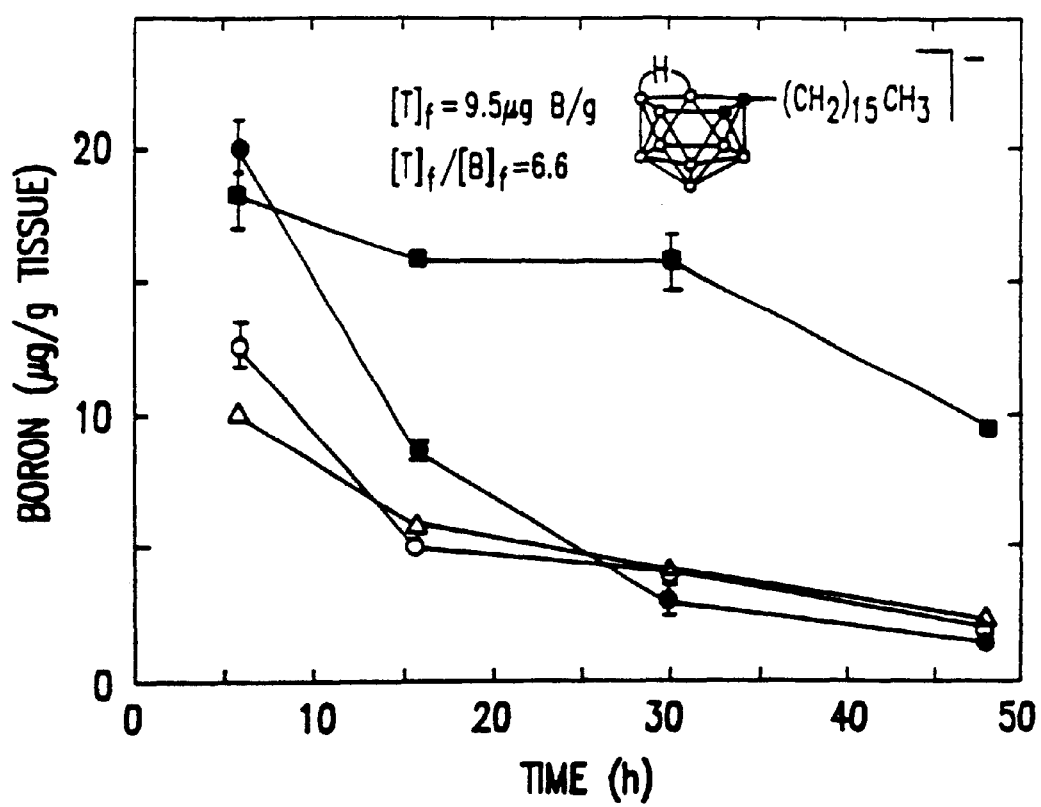
FIG. 14 shows the biodistribution of liposomal $K[CH_3(CH_2)_{15}C_2B_9H_{11}]$ in BALB/c mice bearing EMT6 tumors.

Biodistribution studies were performed on carborane embedded liposomes. With reference to FIG. 14, an isotonic buffer, i.e., phosphate buffered lactose is encapsulated in the internal space of liposomes doped with K[CH$_3$(CH$_2$)$_{15}$ C$_2$B$_9$H$_{11}$], an example of carborane species (a). The 6 hour tumor value is approximately 18 micrograms of boron per gram of tumor. This boron concentration is maintained over a period of 30 hours and then begins to decrease, resulting in a final tumor boron concentration of 9.5 micrograms boron per gram of tumor and a final tumor to blood boron ratio of 6.6.

Figure 15:
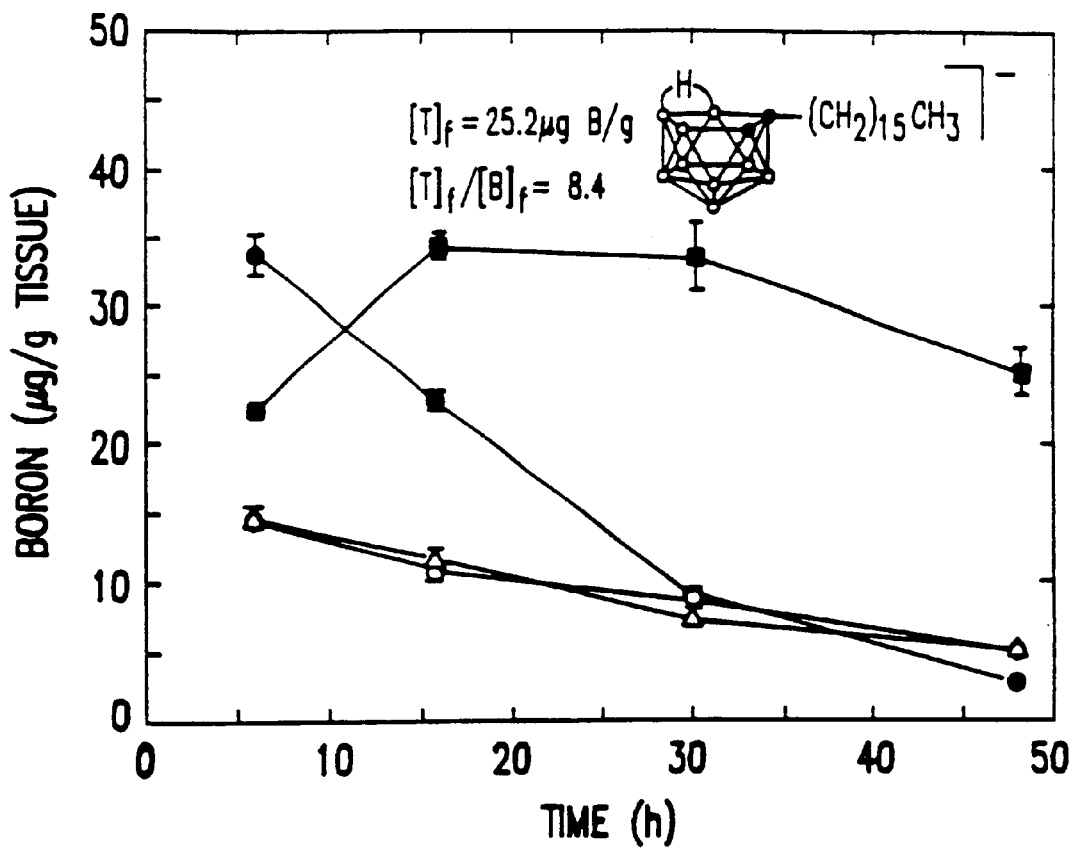
FIG. 15 shows the biodistribution of liposomal $K[CH_3(CH_2)_{15}C_2B_9H_{11}]$ in BALB/c mice bearing EMT6 tumors.

With reference to FIG. 15, a hypertonic buffer (375 mM NaCl/10% HEPES buffer) is encapsulated in the aqueous core (or internal space) of liposomes doped with K(C$_2$B$_9$H$_{11}$)(CH$_2$)$_{15}$CH$_3$. The hypertonic buffer more closely mimics the actual osmotic stress on the liposomes resulting from encapsulated borane solutions. The mean diameter of the liposomes (99 nm) is within the normal range of liposomes desired for BNCT. The injected dose of these liposomes (6.3 mg/kg body weight) is slightly higher than the isotonic buffer example of FIG. 14. The 6 hour tumor value is approximately 22 μg boron/g tumor. This boron concentration increases for approximately 12 hours and then decreases over the remaining time period, resulting in a final tumor boron concentration of 25.2 μg boron/g tumor and a final tumor to blood boron ratio of 8.4, both of which are well within therapeutic values (20 μg boron/g tumor and a tumor to blood boron ratio of 3).

In both FIG. 14 and FIG. 15, the liver and spleen boron concentrations are significantly lower than observed in other in vivo biodistributions.

Another aspect of the present invention involves treating tumors by administering to the patient a therapeutically effective amount of a unilamellar liposome having at least one encapsulating bilayer and an internal space defined by the encapsulating bilayer wherein a carborane, such as of species (a)–(e) or mixtures thereof, is embedded in the bilayer. In another aspect of the present invention, the carborane embedded liposomes as discussed above include a borane compound within the internal space of the liposome. This will increase the amount of $^{10}$B available for BNCT when a borane encapsulated liposome is used. The encapsulated borane compounds can be selected from the borane species discussed above, namely X$_y$B$_{20}$H$_{17}$L and X$_s$B$_{10}$H$_9$L, or other drugs to be delivered to the tumor. Most preferably, the borane is selected from the group consisting of Na$_y$B$_{20}$H$_{17}$NH$_3$ where Y is 1 or 3, and Na$_2$B$_{10}$H$_9$NCO. The method of treating tumors according to this aspect of the present invention comprises administering the carborane embedded liposomes discussed above and exposing the tumors to thermal neutrons.

In all methods according to the present invention, the compounds are administered by i.v. injection with tumor concentration monitored by sacrifice at selected time points. Preferably, the initial boron tumor concentration is at least 10 μg/g tumor, preferably from 20 to 30, but the highest possible concentration is desired. If the desired boron tumor concentration is not up to therapeutic concentration, the pharmaceutical suspension containing the boron agent can be infused over a long period of time or given by multiple injection.

Although this invention has been described with reference to particular applications, the principals involved are susceptible to other applications which will be apparent to those skilled in the art. The invention is accordingly to be limited only by the scope of the appended claims.

the embodiments of the invention in which an exclusive property or privilege is claimed are defmed as follows:

What is claimed:

1. A liposome having one or more encapsulating bilayers and an internal space defined by the encapsulating bilayer wherein a carborane is emdedded in the bilayer of the liposome.

2. The liposome of claim 1 wherein there is present from 0.05 to 20 percent by weight of boron in the liposome bilayers.

3. The liposome of claim 1 wherein there is present from 0.5 to 10 percent by weight of boron in the liposome bilayers.

4. The liposome of claim 1 wherein the bilayers comprise DSPC and cholesterol.

5. The liposome of claim 4 wherein the mole percent ratio of DSPC to cholesterol ranges from 1:1 to 3:1.

6. The liposome of claim 1 wherein the bilayers comprise a phospholipid.

7. The liposome of claim 6 wherein the bilayers further comprise cholesterol.

8. The liposome of claim 1 wherein the carborane is selected from the group consisting of:

a. a carborane of the formula:

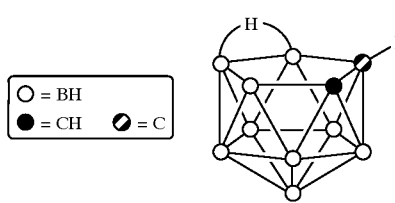

and wherein X is selected from the group consisting of alkali metals and tetra alkyl ammonium, and R is a lipophilic alkyl group;

b. a carborane of the formula

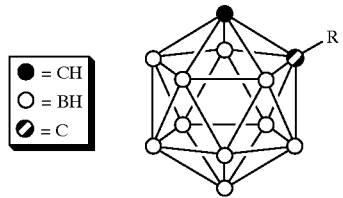

and wherein R is a lipophilic alkyl group;

c. a carborane of the formula:

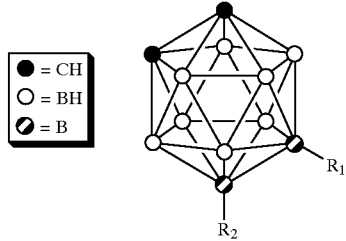

and wherein $R_1$ and $R_2$ are the same or different and are a lipophilic alky group, or $R_1$ or $R_2$ is H and the other of $R_1$ or $R_2$ is a lipophilic alkyl group; and d. a carborane of the formula

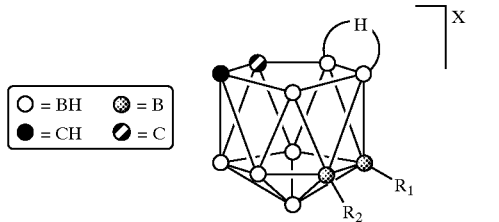

wherein X is selected from the group consisting of alkali metals and tetra alkyl ammonium, and wherein $R_1$ and $R_2$ are the same or different and are a lipophilic alkyl group, or $R_1$ or $R_2$ is H and the other of $R_1$ or $R_2$ is a lipophilic alkyl group.

9. The liposome of claim 8 wherein R, $R_1$ and $R_2$ are —$(CH_2)_xCH_3$ and X ranges from 11 to 19.

10. The liposome of claim 9 wherein R is n-$C_{16}H_{33}$.

11. The liposome of claim 8 wherein $R_1$ and $R_2$ are n-$C_{18}H_{37}$.

12. The liposome of claim 1 wherein the carborane is

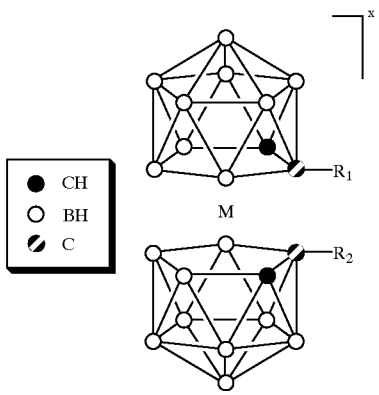

where M is selected from $Fe^{III}$, $Cr^{III}$ and $Co^{III}$ and $R_1$ and $R_2$ are the same or different lipophilic alkyl groups.

13. The liposome of claim 12 wherein $R_1$ and $R_2$ are —$(CH_2)_xCH_3$ and X ranges from 11 to 19.

14. The liposome of claim 13 wherein $R_1$ and $R_2$ are n-$C_{16}H_{33}$.

15. The liposome of claim 13 wherein $R_1$ and $R_2$ are n-$C_{18}H_{37}$.

16. The liposome of claim 1 wherein the carborane is

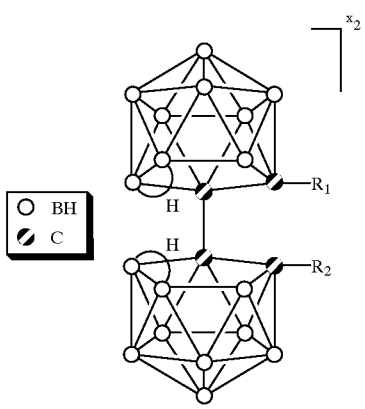

wherein $R_1$ and $R_2$ are the same or different lipophilic alkyl groups.

17. The liposome of claim 16 wherein $R_1$ and $R_2$ are —$(CH_2)_xCH_3$ and X ranges from 11 to 19.

18. The liposome of claim 17 wherein $R_1$ and $R_2$ are n-$C_{16}H_{33}$.

19. The liposome of claim 17 wherein $R_1$ and $R_2$ are n-$C_{18}H_{37}$.

20. The liposome of claim 1 wherein the carborane is

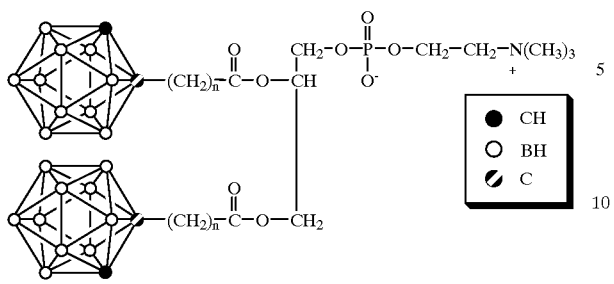

where n is 12, 14, 16, or 18.

21. The liposome of claim 1 having carboranes embedded in the bilayer, said liposome also having carboranes within the internal space.

22. The liposome of claim 21 wherein the borane compound is silected from the group consistion of a. $XB_{20}H_{17}L$, wherein X is selected from the group considing of alkali metals and tetra ammonium and L is any 2 electron donor;

b. $X_sB_{10}H_9L$, wherein X is selected from the group consisting of alkali metal and tetra alkyl ammonium, s is 1 or 2 and L is any 2 electron donor; and c. mixtures of (a) and (b).

23. The liposome of claim 21 wherein the borane is seclected from the group consisting of $Na_yB_{20}H_{17}NH_3$ where y is 1 or 3, and $Na_2B_{10}H_9NCO$.

24. The liposome of claim 22 wherein the carboranes are selected from the group consisting of:

a.

a carborane of the formula:

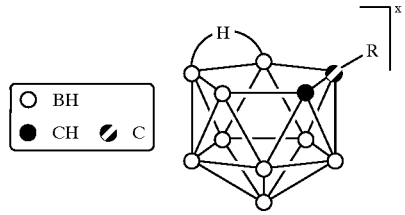

and wherein X is selected from the group consisting of alkali metals and tetra alkyl ammonium, and R is a lipophlic alkyl group;

b.

a carborane of the formula;

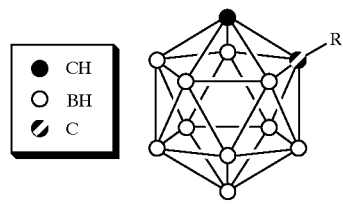

and wherein R is a lipophilic alkyl group;

c.

a carborane of the formula:

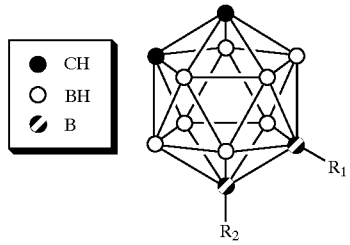

and wherein $R_1$ and $R_2$ are the same or different and are a lipophilic alkyl group, or $R_1$ or $R_2$ is H and the other of $R_1$ or $R_2$ is a lipophilic alkyl group;

d.

a carborane of the formula

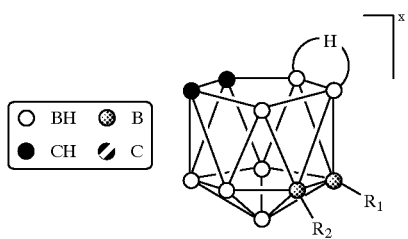

wherein X is selected from the group consisting of alkali metals and tetra alkyl ammonium, and wherein $R_1$ and $R_2$ are the same or different and are a lipophilic alkyl group, or $R_1$ or $R_2$ is H and the other of $R_1$ or $R_2$ is a lipophilic alkyl group, e.

a carborane of the formula

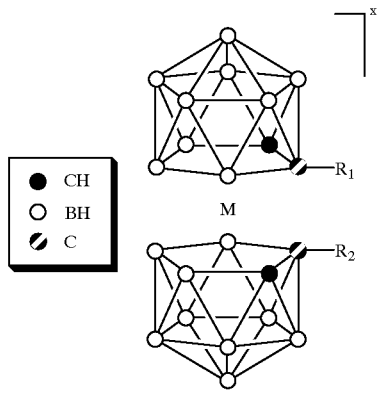

where M is selected from $Fe^{III}$, $Cr^{III}$ and $Co^{III}$ and $R_1$ and $R_2$ are the same or different lipophilic alkyl groups;
a carborane of the formula
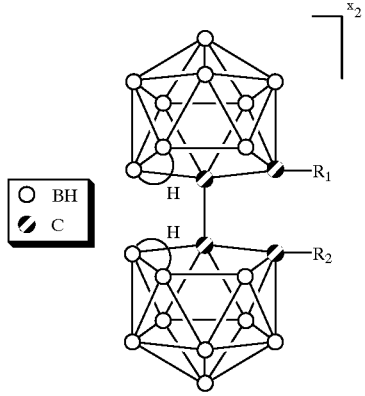
f. a carborane of the formula
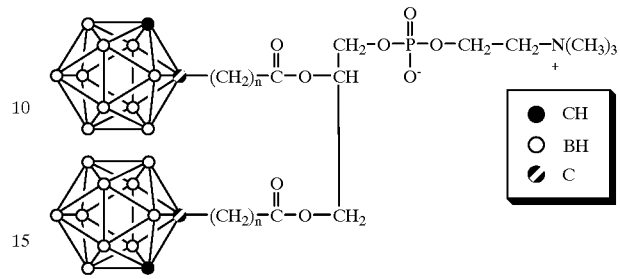
where n is 12, 14, 16, or 18.
wherein $R_1$ and $R_2$ are the same or different lipophilic alkl groups; and
g.
* * * * *